(12) United States Patent
Meijer et al.

(10) Patent No.: US 12,242,190 B2
(45) Date of Patent: Mar. 4, 2025

(54) PHOTOACID GENERATOR FOR CHEMICALLY AMPLIFIED PHOTORESISTS

(71) Applicant: International Business Machines Corporation, Armonk, NY (US)

(72) Inventors: Gerhard Ingmar Meijer, Zurich (CH); Valery Weber, Gattikon (CH); Peter Willem Jan Staar, Zurich (CH)

(73) Assignee: International Business Machines Corporation, Armonk, NY (US)

( * ) Notice: Subject to any disclaimer, the term of this patent is extended or adjusted under 35 U.S.C. 154(b) by 649 days.

(21) Appl. No.: 17/215,363

(22) Filed: Mar. 29, 2021

(65) Prior Publication Data

US 2022/0308448 A1 Sep. 29, 2022

(51) Int. Cl.
| | |
|---|---|
| *G03F 7/004* | (2006.01) |
| *C07C 309/29* | (2006.01) |
| *C07C 381/12* | (2006.01) |
| *G03F 7/20* | (2006.01) |

(52) U.S. Cl.
CPC .......... *G03F 7/0045* (2013.01); *C07C 309/29* (2013.01); *C07C 381/12* (2013.01); *G03F 7/2004* (2013.01)

(58) Field of Classification Search
CPC ... G03F 7/0045; G03F 7/2004; C07C 309/29; C07C 381/12
See application file for complete search history.

(56) References Cited

U.S. PATENT DOCUMENTS

| | | | |
|---|---|---|---|
| 7,718,753 B2 | 5/2010 | Capehart | |
| 7,863,402 B2 | 1/2011 | Capehart | |
| 8,039,194 B2 | 10/2011 | Glodde | |
| 8,343,706 B2 | 1/2013 | Liu | |
| 11,846,886 B2 | 12/2023 | Meijer | |
| 2009/0004601 A1* | 1/2009 | Akita | G03F 7/0392 430/286.1 |
| 2009/0181319 A1 | 7/2009 | Li | |
| 2014/0080062 A1* | 3/2014 | Thackeray | G03F 7/0392 430/296 |
| 2018/0118968 A1* | 5/2018 | Kaur | G03F 7/2041 |

OTHER PUBLICATIONS

Masatoshi Kidowaki and Nobuyuki Tamaoki, Unique crystal structures of donor-acceptor complexes crossed arrangement of two charge-transfer columns, Chem. Commun., 2003, 290-291, Published: Dec. 19, 2002 (Year: 2002).*

(Continued)

*Primary Examiner* — Sean M DeGuire
*Assistant Examiner* — Richard David Champion
(74) *Attorney, Agent, or Firm* — Joseph P. Curcuru

(57) ABSTRACT

In an approach to improve the field of photoacid generators (PAGs) through a new photoacid generator, in particular to a photoacid generator comprising a new polycyclic aromatic photoacid generator compound anion, and a photoresist composition, comprising said photoacid generator. Embodiments the present invention relate to a method of generating an acid using said photoresist composition and a method of forming a patterned materials feature on a substrate.

19 Claims, 18 Drawing Sheets

(56) References Cited

OTHER PUBLICATIONS

Ayothi et al., "New PFOS free photoresist systems for EUV lithography", Journal of Photopolymer Science and Technology, vol. 19, No. 4 (2006),(<https://www.jstage.jst.go.jp/article/photopolymer/19/4/19_4_515/_pdf/-char/en>, 6 pages.

Glodde et al., "Fluorine-free Photoacid Generators for 193nm Lithography Based on Non-Sulfonate Organic Superacids", Journal of Photopolymer Science and Technology, vol. 23, No. 2 (2010), 12 pages.

Wang et al., "Novel anionic photoacid generators (PAGs) and corresponding PAG bound polymers for sub-50 nm EUV lithography", Journal of Materials Chemistry, published Feb. 5, 2007, 8 pages.

* cited by examiner

PHOTOACID GENERATOR FOR CHEMICALLY AMPLIFIED PHOTORESISTS

BACKGROUND

The present invention relates to the field of photoacid generators (PAGs). More specifically, the present invention relates to a new photoacid generator, particularly a photoacid generator comprising a polycyclic aromatic photoacid generator compound anion, and a photoresist composition, comprising said photoacid generator. Finally, the present invention relates to a method of generating an acid using said photoresist composition and a method of forming a patterned materials feature on a substrate.

Photoresists are photosensitive films for the transferring of patterns to a substrate. They form negative or positive patterns. After coating a photoresist on a substrate, a source of activating energy, such as ultraviolet light, is used to project a patterned mask or reticle, typically using a so-called stepper and a scanning objective lens (4x) reduction lens assembly, onto the coating to form a latent pattern in the photoresist coating. The patterned mask defines the pattern desired to be transferred to the underlying substrate.

Chemical amplification-type photoresists have proven to be useful in achieving high sensitivity in processes for forming patterns with small feature sizes in semiconductor manufacturing. These photoresists are prepared by blending a photoacid generator with a polymer matrix having acid labile structures. According to the reaction mechanism of such a photoresist, the photoacid generator generates acid when it is irradiated by the light source, and the main chain or branched chain of the polymer matrix in the exposed or irradiate portion reacts with the generated acid and is decomposed or cross-linked, so that the polarity of the polymer is altered. This alteration of polarity results in a solubility difference in the developing solution between the irradiated exposed area and the unexposed area, thereby forming a positive or negative pattern of a mask on the substrate.

SUMMARY

Embodiments disclose a polycyclic aromatic photoacid generator compound anion of a general formula, wherein the general formula comprises (first benzene moiety-X-second benzene moiety)$^-$, and wherein: X represents a central cycle; the first benzene moiety is substituted with a first sulfonate group and the second benzene moiety is substituted with a second sulfonate group; or the first benzene moiety is substituted with a sulfonate group and the second benzene moiety is substituted with a sulfonic acid group; and the first sulfonate group and the second sulfonate group or the first sulfonate group and the sulfonic acid group are arranged on said first and second benzene moiety such that their orbitals can interact with each other.

In another aspect, the present invention relates to a photoacid generator comprising the photoacid generator compound anion according to the present invention and a cation.

In another aspect, the present invention relates to a photoresist composition comprising: a photoacid generator according to the present invention; and an acid labile polymer.

In a further aspect, the present invention relates to a method for generating an acid, comprising: applying a photoresist composition according to the present invention to a substrate, the photoresist composition containing a photoacid generator according to the present invention, and irradiating the photoresist composition with an energy ray to cause the photoacid generator to generate an acid.

Finally, in a still further aspect, the present invention relates to a method of forming a patterned materials feature on a substrate, comprising: providing a material surface on a substrate; forming a layer of the photoresist composition according to the present invention over said material surface; patternwise irradiating the photoresist layer with an energy ray thereby creating a pattern of radiation-exposed regions in said photoresist layer; selectively removing portions of said photoresist layer to form exposed portions of said material surface; and etching or ion implanting said exposed portions of said material, thereby forming said patterned material feature.

Surprisingly, it has been discovered that the PAG compound anions of the present disclosure are characterized by excellent photoreactivity for DUV and for EUV radiation.

The new PAG comprising the new polycyclic aromatic photoacid generator compound anion generates upon UV exposure a fluorine free acid that may have a high acid dissociation constant.

The chemically amplified photoresist for DUV and for EUV lithography that comprise the new PAG comprising the new polycyclic aromatic photoacid generator compound anion may have a material's toxicity and chemical waste advantage.

The chemically amplified photoresist for EUV lithography that comprise the new PAG comprising the new polycyclic aromatic photoacid generator compound anion may have a high absorption cross section for photons in the EUV to increase the sensitivity for EUV lithography.

The chemically amplified photoresist for EUV lithography that comprise the new PAG comprising the new polycyclic aromatic photoacid generator compound anion may pose limited process-integration risks because the process flow in the fab's photobay is unchanged.

Various variants provide a photoacid generator compound anion, a photoacid generator, a photoresist composition and methods, as described by the subject matter of the independent claims. Advantageous variants are described in the dependent claims. Embodiments of the present invention can be freely combined with each other if they are not mutually exclusive.

DETAILED DESCRIPTION

Figure 1:
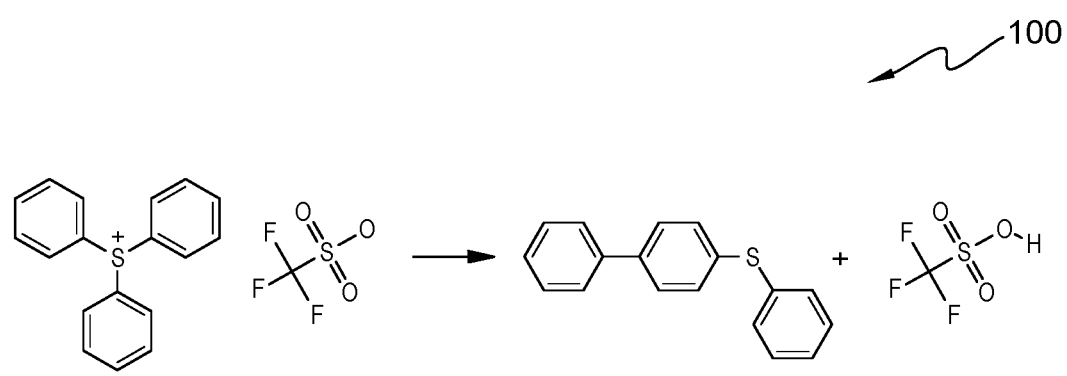
FIG. 1 depicts a PAG triphenylsulfonium trifluoromethanesulfonate decomposition with trifluoromethanesulfonic acid generation according to one embodiment.

The descriptions of the various embodiments of the present invention will be presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Unless otherwise stated, the following terms used in this application, including the specification and claims, have the definitions given below. It must be noted that, as used in the specification and the appended claims, the singular forms "a," "an," and "the" include plural referents unless the context clearly dictates otherwise.

As used herein, the term "comprising" means that the named components are essential, but other components may be added and are still embraced by a composition.

As used herein, the term "consisting of" as used according to the present invention means in general that the total amount of components of a composition adds up to 100% by weight, based on the total weight of the composition, and signifies that the subject matter is closed-ended and can only include the limitations that are expressly recited.

Whenever reference is made to "comprising" it is intended to cover both meanings as alternatives, that is the meaning can be either "comprising" or "consisting of," unless the context dictates otherwise.

As used herein, the term "moiety" refers to a specific segment or functional group of a molecule. Chemical moieties are often recognized chemical entities embedded in or appended to a molecule.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing from 1 to 20 (e.g., 2 to 18, 3 to 18, 1 to 8, 1 to 6, 1 to 4, or 1 to 3) carbon atoms. An alkyl group can be straight, branched, cyclic or any combination thereof. Examples of alkyl groups comprise, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents or can be multicyclic as set forth below.

Unless specifically limited otherwise, the term "alkyl," as well as derivative terms such as "alkoxy" and "thioalkyl," as used herein, comprise within their scope, straight chain, branched chain, and cyclic moieties.

As used herein, an "alkenyl" group refers to an aliphatic carbon group that contains from 2 to 20 (e.g., 2 to 18, 2 to 8, 2 to 6, or 2 to 4) carbon atoms and at least one double bond. Like an alkyl group, an alkenyl group can be straight, branched or cyclic or any combination thereof.

Examples of an alkenyl group comprise, but are not limited to, allyl, isoprenyl, 2-butenyl, and 2-hexenyl. An alkenyl group can be optionally substituted with one or more substituents as set forth below.

As used herein, an "alkynyl" group refers to an aliphatic carbon group that contains from 2 to 20 (e.g., 2 to 8, 2 to 6, or 2 to 4) carbon atoms and has at least one triple bond. An alkynyl group can be straight, branched or cyclic or any combination thereof. Examples of an alkynyl group comprise, but are not limited to, propargyl and butynyl. An alkynyl group can be optionally substituted with one or more substituents as set forth below.

As used herein, the term "alicyclic" refers to an aliphatic ring compound or group comprising at least three carbon atoms and the bonds between pairs of adjacent atoms may all be of the type designated single bonds (involving two electrons), or some of them may be double or triple bonds (with four or six electrons, respectively).

A "halogen" is an atom of the group 17 of the periodic table of elements, which includes fluorine, chlorine, bromine, and iodine.

As used herein, an "aryl" group refers to an aromatic ring compound or group having 3 to 30 carbon atoms and used alone or as part of a larger moiety as in "aralkyl," "aralkoxy," or "aryloxyalkyl" and refers to monocyclic (e.g., phenyl); bicyclic (e.g., indenyl, naphthalenyl, tetrahydronaphthyl, or tetrahydroindenyl); and tricyclic (e.g., fluorenyl, tetrahydrofluorenyl, tetrahydroanthracenyl, or anthracenyl) ring systems in which the monocyclic ring system is aromatic or at least one of the rings in a bicyclic or tricyclic ring system is aromatic. The bicyclic and tricyclic groups include benzofused 2 to 3 membered carbocyclic rings. For example, a benzofused group includes phenyl fused with two or more $C_4$ to $C_8$ carbocyclic moieties. An aryl is optionally substituted with one or more substituents as set forth below.

As used herein, an "aralkyl" or "arylalkyl" group refers to an alkyl group (e.g., a $C_1$ to $C_4$ alkyl group) that is substituted with an aryl group. Both "alkyl" and "aryl" have been defined above. An example of an aralkyl group is benzyl. An aralkyl is optionally substituted with one or more substituents as set forth below.

As used herein, a "cycloalkyl" group refers to a saturated carbocyclic mono- to pentacyclic (fused or bridged) ring of 3 to 20 (e.g., 5 to 20) carbon atoms. Examples of cycloalkyl groups include cyclopropyl, cyclobutyl, cyclopentyl, cyclohexyl, cycloheptyl, adamantyl, norbornyl, cubyl, octahydroindenyl, decahydro-naphthyl, bicyclo[3.2.1]octyl, bicyclo[2.2.2]octyl, bicyclo[3.3.1]nonyl, bicyclo[3.3.2]decyl, bicyclo[2.2.2]octyl, adamantyl, azacycloalkyl, or ((aminocarbonyl)cycloalkyl) cycloalkyl.

As used herein, the term "heteroaryl" group refers to a monocyclic, bicyclic, or tricyclic ring system having 3 to 30 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents as is set forth below.

A "heteroarylalkyl" group, as used herein, refers to an alkyl group (e.g., a $C_1$ to $C_4$ alkyl group) that is substituted with a heteroaryl group. Both "alkyl" and "heteroaryl" have been defined above. A heteroarylalkyl is optionally substituted with one or more substituents as is set forth below.

As used herein, an "acyl" group refers to a formyl group or $R^X$—C(O)— (such as -alkyl-C(O)—, also referred to as "alkylcarbonyl") where "alkyl" has been defined previously.

As used herein, the term "acyloxy" includes straight-chain acyloxy, branched-chain acyloxy, cycloacyloxy, cyclic acyloxy, heteroatom-unsubstituted acyloxy, heteroatom-substituted acyloxy, heteroatom-unsubstituted $C_n$-acyloxy, heteroatom-substituted $C_n$-acyloxy, alkylcarbonyloxy, arylcarbonyloxy, alkoxycarbonyloxy, aryloxycarbonyloxy, and carboxylate groups.

As used herein, an "alkoxy" group refers to an alkyl-O— group where "alkyl" has been defined previously.

As used herein, a "carboxy" group refers to —COH, —COOR$^X$, OC(O)H, OC(O)R$^X$ when used as a terminal group; or —OC(O)— or —C(O)O— when used as an internal group.

As used herein, "alkoxycarbonyl" means —COOR where R is alkyl as defined above, e.g., methoxycarbonyl, ethoxycarbonyl, and the like.

As used herein, a "sulfonate" group refers to R—S(O)$_2$—O$^-$ when used terminally. Sulfonates are the conjugate base of sulfonic acids with the general formula R—S(O)$_2$—OH.

As used herein, a "sulfonic acid" group refers to R—S(O)$_2$—OH when used terminally.

As used herein, a "sulfinyl" group refers to —S(O)—R$^X$ when used terminally or —S(O)— when used internally.

As used herein, a "sulfonyl" group refers to —S(O)$_2$—R$^X$ when used terminally or —S(O)$_2$— when used internally.

The term "alkylthio" includes straight-chain alkylthio, branched-chain alkylthio, cycloalkylthio, cyclic alkylthio, heteroatom-unsubstituted alkylthio, heteroatom-substituted alkylthio, heteroatom-unsubstituted $C_n$-alkylthio, and heteroatom-substituted $C_n$-alkylthio. In certain embodiments, lower alkylthios are contemplated.

As used herein, the term "amine" or "amino" includes compounds where a nitrogen atom is covalently bonded to at least one carbon or heteroatom. The term "amine" or "amino" also includes —NH$_2$ and also includes substituted moieties. The term includes "alkyl amino" which comprises groups and compounds wherein the nitrogen is bound to at least one additional alkyl group. The term includes "dialkyl amino" groups wherein the nitrogen atom is bound to at least two additional independently selected alkyl groups. The term includes "arylamino" and "diarylamino" groups wherein the nitrogen is bound to at least one or two independently selected aryl groups, respectively.

The term "haloalkyl" refers to alkyl groups substituted with from one up to the maximum possible number of halogen atoms. The terms "haloalkoxy" and "halothioalkyl" refer to alkoxy and thioalkyl groups substituted with from one up to five halogen atoms.

The phrase "optionally substituted" is used interchangeably with the phrase "substituted or unsubstituted." As described herein, compounds of the present disclosure can optionally be substituted with one or more substituents, such as are illustrated generally above, or as exemplified by particular classes, subclasses, and species of the present disclosure. As described herein any of the above moieties or those introduced below can be optionally substituted with one or more substituents described herein. Each substituent of a specific group is further optionally substituted with one to three of halogen, cyano, oxoalkoxy, hydroxy, amino, nitro, aryl, haloalkyl, and alkyl. For instance, an alkyl group can be substituted with alkyl sulfonyl and the alkyl sulfonyl can be optionally substituted with one to three of halogen, cyano, oxoalkoxy, hydroxy, amino, nitro, aryl, haloalkyl, and alkyl.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this present disclosure are those combinations that result in the formation of stable or chemically feasible compounds.

Modifications or derivatives of the compounds disclosed throughout this specification are contemplated as being useful with the methods and compositions of the present disclosure. Derivatives may be prepared and the properties of such derivatives may be assayed for their desired properties by any method known to those of skill in the art. In certain aspects, "derivative" refers to a chemically modified compound that still retains the desired effects of the compound prior to the chemical modification.

Embodiments of the present invention recognize that deep ultraviolet (DUV) and extreme ultraviolet (EUV) lithography are being used as technology for semiconductor manufacturing of next generation devices. DUV lithography is the process of defining a pattern in a thin photosensitive polymer layer (photoresist) using controlled 193 nm or 248 nm light, which corresponds to an energy of about 6 eV or 5 eV, respectively, such that the resulting polymer pattern can be transferred into or onto the underlying substrate by etching, deposition, or implantation. EUV lithography is a technology platform that uses an EUV ray having a wavelength of about 13.5 nm, which corresponds to an energy of about 92 eV, as an exposure light source. Embodiments of the present invention recognize that with the help of the EUV lithography, patterns with very small feature sizes (e.g., patterns having a width or critical dimension of less than or equal to about 20 nm) may be formed in an exposure process during a manufacturing of a semiconductor device.

Embodiments of the present invention recognize that State of the art photoresists for DUV and for EUV lithography of the 7-nm and 5-nm technology nodes are polymer-based chemically amplified photoresists. These photoresist platforms comprise the following components: (i) photoacid generator: The PAG decomposes upon ultraviolet (UV) exposure; an acid is generated along with degradation products. Commonly used PAGs are based on sulfonium salts, for example, triphenylsulfonium trifluoromethanesulfonate. upon UV exposure, the sulphur-carbon (S—C) bond in the sulfonium salts undergoes radical cleavage and an acid is generated; and (ii) acid-labile polymer: Embodiments of the present invention recognize that the acid-labile protection group of this polymer can be removed by an acid, wherein the thereby generated compounds are alkali-soluble or volatile.

Commonly used PAGs are based on sulfonium salts with a fluorinated anion. FIG. 1, chemical reaction diagram 100, depicts a PAG triphenylsulfonium trifluoromethanesulfonate decomposition with trifluoromethanesulfonic acid generation, according to one embodiment, which is a reference benchmark. Upon UV exposure, the C—S bond in the sulfonium salt undergoes radical cleavage and trifluoromethanesulfonic acid is generated.

The halogen fluorine is known to be a strong electron-withdrawing element. Embodiments of the present invention recognize that halogen flourine utilized to devise PAGs that upon UV exposure generate acids with a high acid dissociation constant. The key property for the functionality of molecules with variable protonation is the acidity. The acidity scale can be described in terms of acid dissociation constant and in terms of proton dissociation energy: a high acid dissociation constant corresponds to a low proton dissociation energy. Commonly used PAGs, which all comprise a fluorinated anion, are displayed in FIG. 2.

Figure 2:
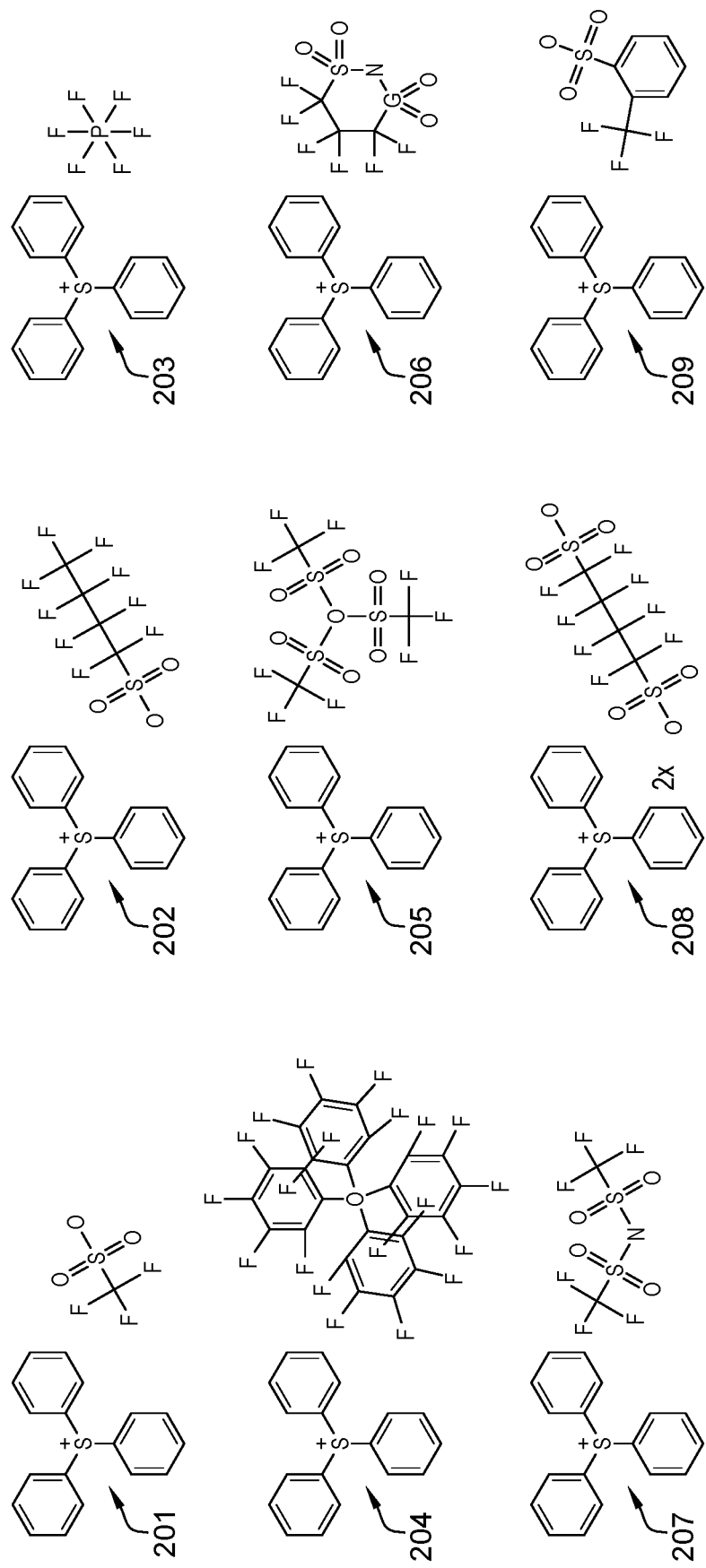
FIG. 2 depicts an example of commonly used PAGs.

FIG. 2 depicts PAGs: (201) triphenylsulfonium trifluoromethanesulfonate, (202) triphenylsulfonium perfluoro-1-butanesulfonate, (203) triphenylsulfonium hexafluorophosphate, (204) triphenylsulfonium tetrakis(pentafluorophenyl) borate, (205) triphenylsulfonium tris(trifluoromethanesulfonyl)methide, (206) triphenylsulfonium hexafluoropropane-1,3-disulfonimide, (207) triphenylsulfonium bis(trifluoromethane-sulfonyl) amide, (208) bis(triphenylsulfonium) perfluorobutane-1,4-disulfonate, and (209) triphenylsulfonium 2-(trifluoromethyl)benzenesulfonate. The PAGs, depicted in FIG. 2, generate upon UV exposure Brønsted acids (or, in some cases, a Lewis acid) with a high acid dissociation constant.

However, embodiments of the present invention recognize that, the photoresist's toxicity and chemical waste are increasingly in focus. Regulation bodies scrutinize used fluorinated materials and international actions on these fluorinated materials are to be expected (see, for example, EU regulatory actions to control and phase-down fluorinated materials such as perfluorocarbons and sulphur hexafluoride as part of its policy). Currently available chemically amplified photoresists for DUV and for EUV lithography have generally, due to the use of PAGs with fluorinated anions, a material's toxicity and chemical waste pain-point.

Alternatives for fluorine as strong electron withdrawing element include the cyano group and the nitro group. Embodiments of the present invention recognize that PAGs with anions comprising cyano groups are known in the art. Upon UV exposure, an acid comprising cyano groups is generated. While these PAGs are fluorine free, materials with cyano groups often have a material's toxicity and chemical waste pain-point too. The usability of the nitro group in PAGs is limited because this group is an explosophore.

Embodiments of the present invention recognize that another key metric of the photoresist is its sensitivity. Sensitivity is the UV dose that is required to print a feature in the photoresist. Currently available chemically amplified photoresists for EUV lithography have generally a too low sensitivity.

Figure 3:
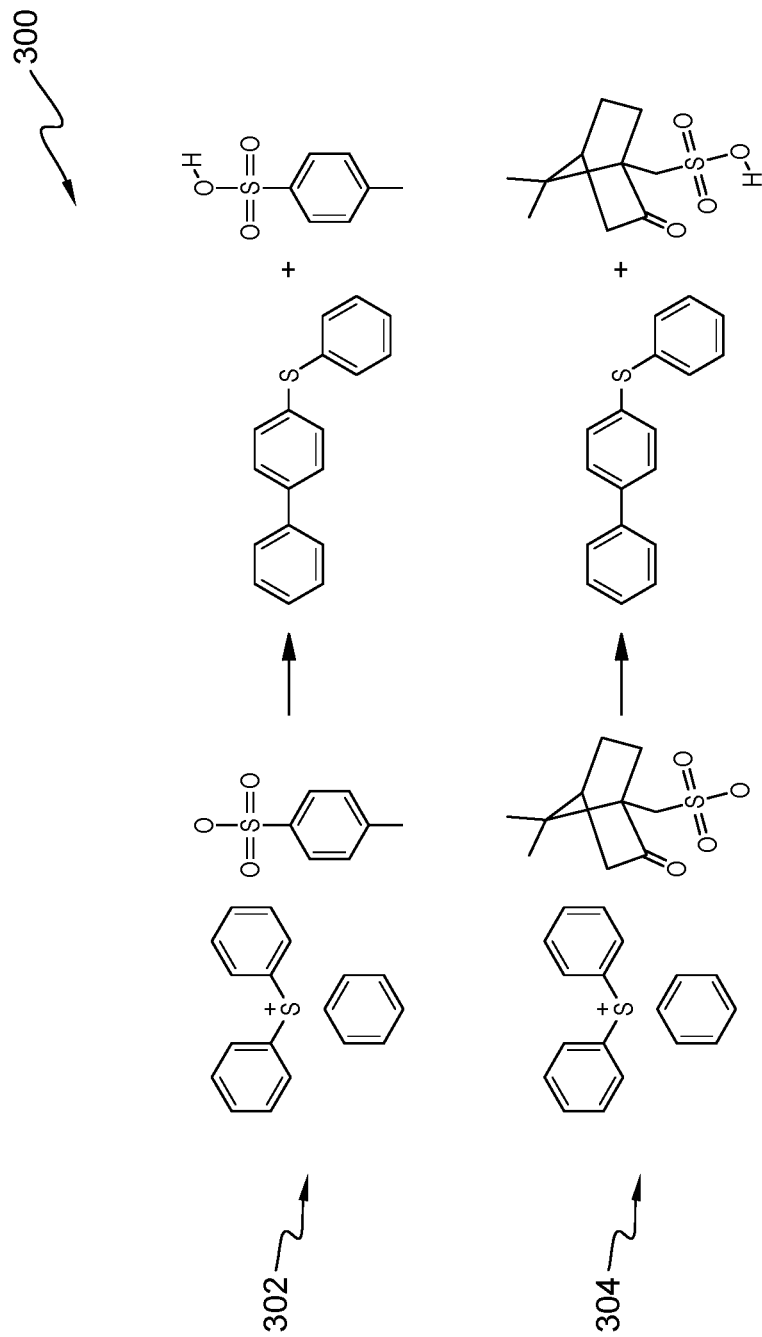
FIG. 3 depicts an example of PAG triphenylsulfonium p-toluenesulfonate decomposition with p-toluenesulfonic acid generation, and PAG triphenylsulfonium camphorsulfonate decomposition with camphorsulfonic acid generation.

Commercially available PAGs with fluorine free anions, which have no material's toxicity and chemical waste pain-point, are displayed in FIG. 3. FIG. 3, chemical reaction diagram 300, depicts PAG triphenylsulfonium p-toluenesulfonate decomposition with p-toluenesulfonic acid generation (302), and PAG triphenylsulfonium camphorsulfonate decomposition with camphorsulfonic acid generation (304). However, the fluorine free acids that these PAGs generate upon UV exposure, p-toluenesulfonic acid and camphorsulfonic acid, have a comparably low acid dissociation constant. For comparison, the acid dissociation constant of p-toluenesulfonic acid and camphorsulfonic acid is about 14 orders of magnitude smaller than that of trifluoromethanesulfonic acid. Therefore, these PAGs are of limited use for chemically amplified photoresists for DUV and for EUV lithography.

Another important challenge is mitigating the process-integration risk of new types of photoresist platforms for EUV lithography.

Accordingly, there is a need to provide PAGs that comprise fluorine free anions which generate upon UV exposure fluorine free acids that have a high acid dissociation constant which is similar to that of trifluoromethanesulfonic acid.

The photoacid generator compound anion according to the present disclosure can be used as photoacid generator as will be explained in more detail below. The term "photoacid generator" means a compound capable of producing an acid by decomposition of its chemical structure when irradiated with light (e.g., UV exposure).

The present invention comprises novel photoacid generators to be formulated into polymer compositions that are useful in lithographic processes, especially when DUV or EUV radiation is used. In carrying out the present invention, conventional materials and processing techniques can be employed and, hence, such conventional aspects are not set forth herein in detail. For example, the selection of suitable acid labile polymers, base quenchers, and solvents is conducted in a conventional manner.

In accordance with the purpose of the present invention as embodied and broadly described herein, the invention may provide a fluorine free photoacid generator compound anion, comprising an aromatic element, a fluorine free aromatic element, comprising two, i.e., a first and a second, benzene moieties connected to a central cycle. A first sulfonate group and a second sulfonate group is each bonded to said first and second benzene moieties. Alternatively, a sulfonate group and a sulfonic acid group is each bonded to said first and second benzene moieties. The first and the second sulfonate groups or the sulfonate group and the sulfonic acid group are arranged on said benzene moieties in such a way that their orbitals can interact with each other. The acid dissociation constant of the acid that is generated upon UV exposure of the PAG can be tuned by modifying the size of said central cycle, and/or by functionalizing said central cycle, and/or by adding substituents to said benzene moieties. In addition, the sensitivity for EUV lithography can be tuned by incorporating elements having a specific absorption cross section for 92 eV photons into the photoacid generator compound anion.

In a first aspect, the present invention relates to a polycyclic aromatic photoacid generator compound anion of the general formula (I), wherein X represents a central cycle; the first benzene moiety is substituted with a first sulfonate group and the second benzene moiety is substituted with a second sulfonate group; or the first benzene moiety is substituted with a sulfonate group and the second benzene moiety is substituted with a sulfonic acid group; and the first sulfonate group and the second sulfonate group or the first sulfonate group and the sulfonic acid group are arranged on said first and second benzene moiety such that their orbitals can interact with each other.

(first benzene moiety-X-second benzene moiety)⁻     Formula (I):

The photoacid generator compound anion of the general formula (I) is characterized in that it comprises a first benzene moiety, a central cycle, and a second benzene moiety. The first benzene moiety and the second benzene moiety are linked to the central cycle in such a manner, that the first benzene moiety, the central cycle, and the second benzene moiety form a condensed ring system, i.e., a polycyclic aromatic hydrocarbon. A polycyclic aromatic hydrocarbon is a chemical compound containing only carbon and hydrogen atoms and is composed of multiple aromatic rings. Polycyclic aromatic hydrocarbons in general are uncharged, non-polar molecules, with distinctive properties due in part to the delocalized electrons in their aromatic rings.

For steric effects, the condensed ring system is a linear condensed ring system, i.e., the rings of the first benzene moiety, the central cycle, and the second benzene moiety are arranged in one line but not arranged angular.

The central cycle of the polycyclic aromatic photoacid generator anion according to general formula (I) is a four membered, a five membered, a six membered, a seven membered, or even an eight membered cycle. In one particular embodiment, the central cycle is a four membered, a five membered or six membered cycle. For steric reasons and for geometrical arrangement optimum, as it is described later, the central cycle is a five membered cycle or a six membered cycle. In an embodiment of the present invention, the central cycle in the polycyclic aromatic photoacid generator anion is a six membered cycle. With a six membered cycle as the central cycle the steric effect of the condensed ring system is the highest.

In one particular embodiment, in the central cycle of the polycyclic aromatic photoacid generator anion according to general formula (I) at least one atom of the central cycle which is not chemically bonded to the first benzene moiety and to the second benzene moiety is a heteroatom selected from the group consisting of O and S.

The term "at least one atom" in the context of the present invention means that the central cycle can include either one heteroatom or can include two or even more identical or different heteroatoms.

In one particular embodiment, the central cycle includes one heteroatom selected from the group consisting of O and S. In some embodiments of the present invention, the central cycle includes two identical or different heteroatoms selected from the group consisting of O and S.

In an alternative variant, the central cycle of the polycyclic aromatic photoacid generator anion according to the general formula (I) can be functionalized by a group selected from the consisting of carbonyl, sulfinyl, and sulfonyl. Said functionalizing group is part of the central cycle and is not chemically bonded to the first and/or second benzene moiety.

In one particular embodiment of the present invention, in the central cycle of the polycyclic aromatic photoacid generator anion according to the general formula (I) one atom of the central cycle which is not chemically bonded to the first benzene moiety and to the second benzene moiety is a heteroatom as described herein and the central cycle of the polycyclic aromatic photoacid generator comprises a functionalizing group as described herein.

In one particular embodiment, the heteroatom and/or functionalizing group is/are part of a five membered or six membered central cycle.

In one particular embodiment, the central cycle of the polycyclic aromatic photoacid generator anion according to the present invention is derived from compounds selected from the group consisting of: cyclobutane, cyclopentane, cyclohexane, cycloheptane, cyclooctane, tetrahydrofuran (five-membered cycle with O), tetrahydrothiophene (five-membered cycle with S), cyclopentanone (five-membered cycle with carbonyl), tetrahydrothiophene-1-oxide (five-membered cycle with sulfinyl), tetrahydrothiophene-1,1-dioxide (five-membered cycle with sulfonyl), tetrahydropyran (six-membered cycle with O), tetrahydrothiopyran (six-membered cycle with S), cyclohexanone (six-membered cycle with carbonyl), tetrahydrothiopyran-1-oxide (six-membered cycle with sulfinyl), tetrahydrothiopyran-1,1-dioxide (six-membered cycle with sulfonyl), 1,4-oxathiane (six-membered cycle with O and S), 4-tetrahydropyranone (six-membered cycle with O and carbonyl), 1,4-oxathiane-4-oxide (six-membered cycle with O and sulfinyl), 1,4-oxathiane-4,4-dioxide (six-membered cycle with O and sulfonyl), 4-tetrahydrothiopyranone (six-membered cycle with S and carbonyl), 1,4-dithiane-1-oxide (six-membered cycle with S and sulfinyl), 1,4-dithiane-1,1-dioxide (six-membered cycle with S and sulfonyl), 1,4-dioxane (six-membered cycle with 2 O), and 1,4-dithiane (six-membered cycle with 2 S).

Figure 4:
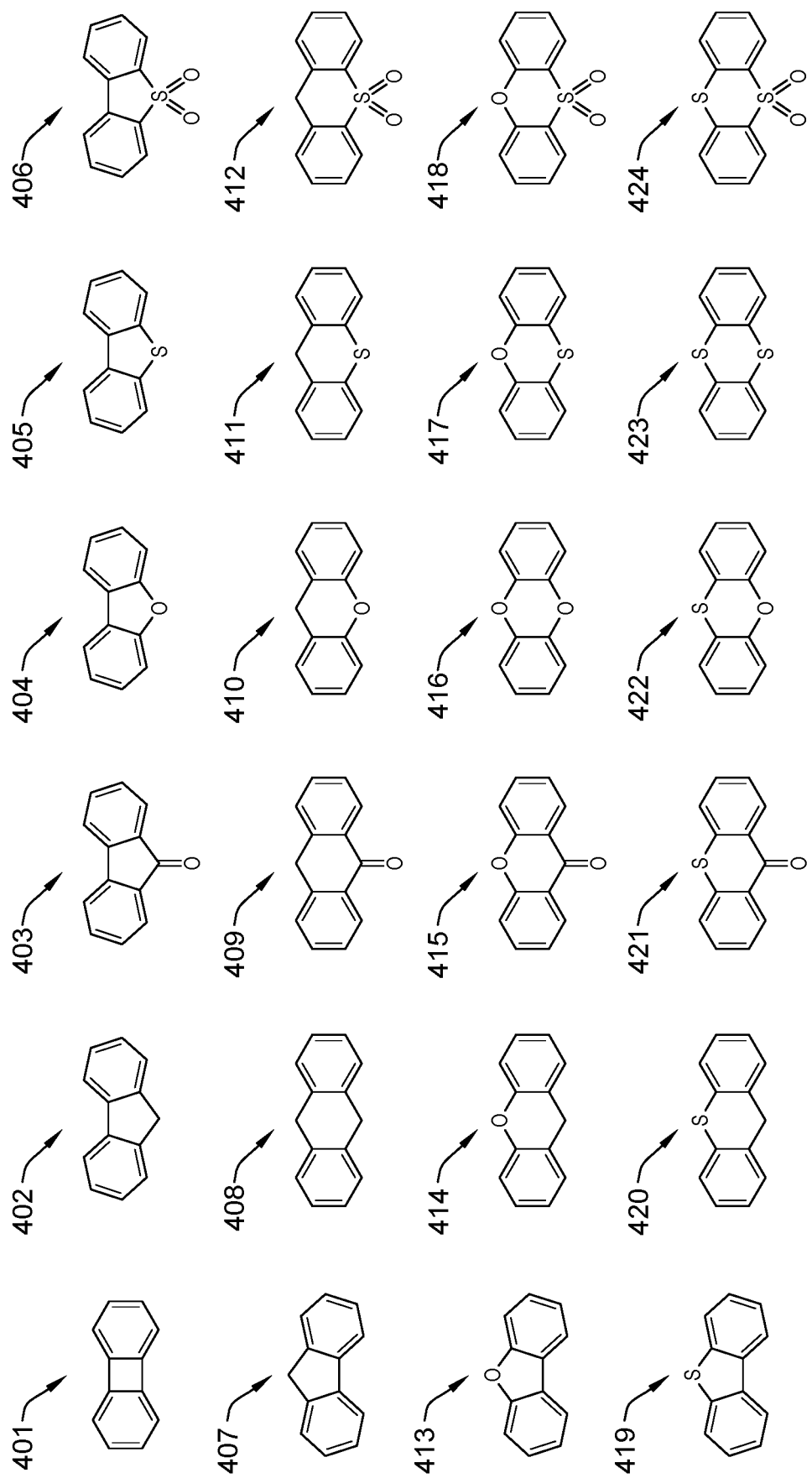
FIG. 4 shows examples of condensed ring systems according to an embodiment of the present invention.

In various embodiment of the present invention of the PAG anion's condensed ring system, i.e., aromatic basis element, of formula (I) according to the present invention are selected from the group consisting of: biphenylene (401), fluorene (402), fluorenone (403), dibenzofuran (404), dibenzothiophene (405), dibenzothiophene-10,10-dioxide (406), fluorene (407), 5,10-dihydroanthracene (408), anthrone (409), xanthene (410), thioxanthene (411), thioxanthene-10,10-dioxide (412), dibenzofuran (413), xanthene (414), xanthone (415), oxanthrene (416), phenoxathiine (417), phenoxathiine-10,10-dioxide (418), dibenzothiophene (419), thioxanthene (420), thioxanthone (421), phenoxathiin (422), thianthrene (423), and thianthrene-5,5-dioxide (424), as depicted in FIG. 4.

The photoacid generator compound anion of the general formula (I) according to the present invention further comprises in a first alternative a first sulfonate group and a second sulfonate group. The first sulfonate group is chemically bonded to the first benzene moiety and the second sulfonate group is chemically bonded to the second benzene moiety.

In a second alternative, the photoacid generator compound anion of the general formula (I) according to the present invention comprises a sulfonate group and a sulfonic acid group. The sulfonate group is chemically bonded to the first benzene moiety and the sulfonic acid group is chemically bonded to the second benzene moiety, or vice versa.

Essentially, the first sulfonate group and the second sulfonate group or the sulfonate group and the sulfonic acid group are arranged on said first and second benzene moiety such that their orbitals can interact with each other. The interaction is a crucial factor for the proton dissociation energy of the acid that is generated upon UV exposure of the PAG. The proton dissociation energy should be similar to or even smaller than that of trifluoromethanesulfonic acid, which is a reference benchmark.

In order to enable that the first sulfonate group and the second sulfonate group or the sulfonate group and the sulfonic acid group can interact with each other, it is decisive that they are in close proximity to each other. For geometrical arrangement optimum, the first sulfonate group and the second sulfonate group or the sulfonate group and the sulfonic acid group are arranged on the same side of the planar of the condensed ring system. By this arrangement, the geometrical arrangement optimum and interaction may be ensured.

If the first sulfonate group and the second sulfonate group or the sulfonate group and the sulfonic acid group are arranged on different sides of the planar of the condensed ring system, the orbitals of the respective groups cannot interact with each other.

In one particular embodiment, the first and the second sulfonate group or the sulfonate group and the sulfonic acid group of the polycyclic aromatic photoacid generator compound anion according to the present invention are arranged on the same side of the planar of the condensed ring system and are linked to the first carbon atom of the first and second benzene moieties adjacent to the central cycle. By such an arrangement, the geometrical arrangement and interaction is optimal, resulting in a proton dissociation energy of the acid that is generated upon UV exposure of the PAG, which is similar to or even smaller than that of trifluoromethanesulfonic acid.

In one particular embodiment of the present invention, the geometrical arrangement is optimal, if the first and the second sulfonate group or the sulfonate group and the sulfonic acid group are arranged on the same side of the planar condensed ring system and are linked to the first carbon atom of the first and second benzene moieties adjacent to the central cycle, and the central cycle is a five membered or six membered cycle. By such an arrangement, the first and the second sulfonate group or the sulfonate group and the sulfonic acid group have the optimum proximity for interacting with each other.

If the first and the second sulfonate group or the sulfonate group and the sulfonic acid group are arranged on the same side of the planar condensed ring system but in too close proximity, for example if the central cycle is a four membered cycle, the proton dissociation energy of the acid that is generated upon UV exposure of the PAG becomes too high and is not similar to that of trifluoromethanesulfonic acid any longer.

Figure 5:
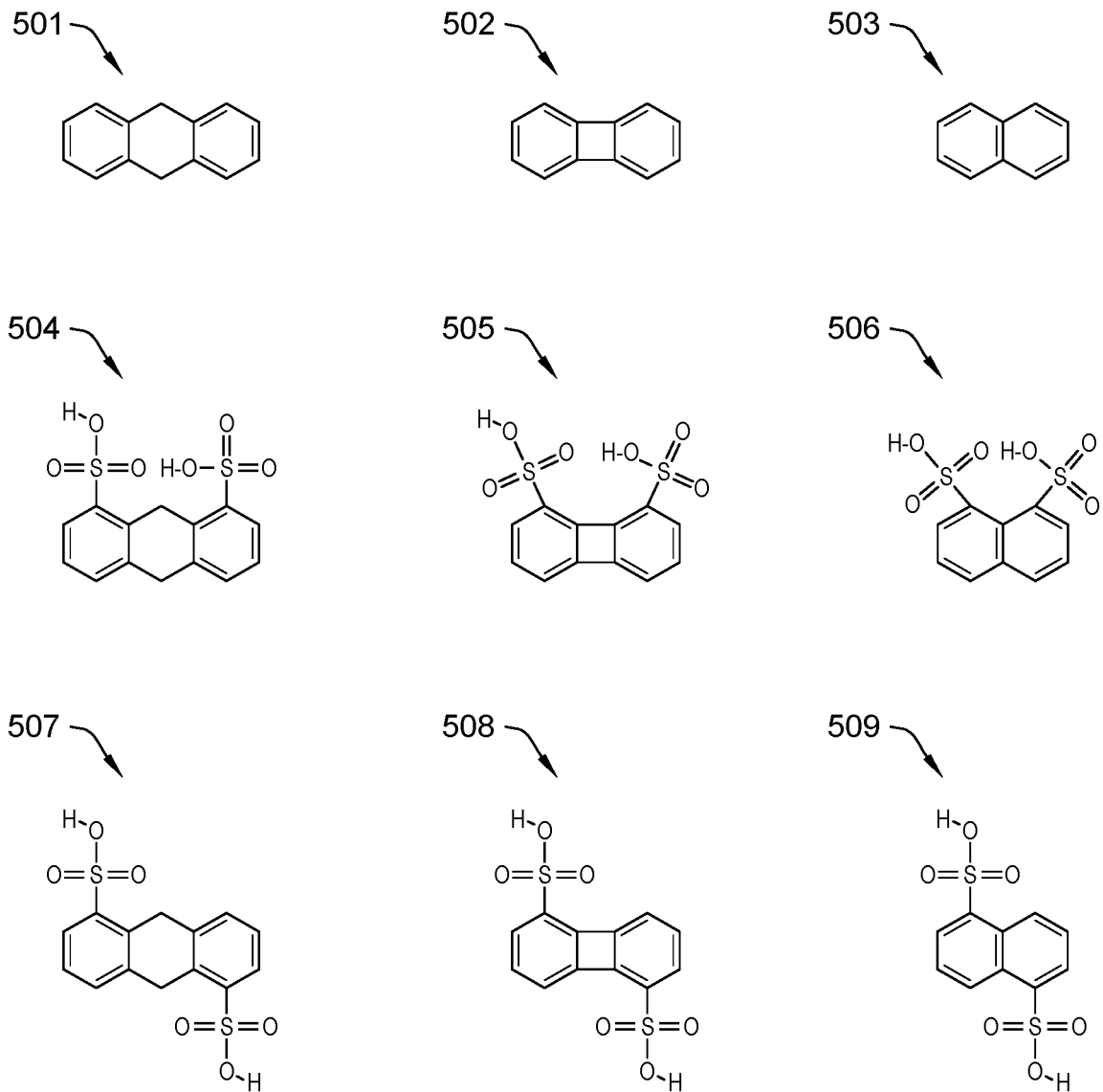
FIG. 5 shows disulfonic acids generated upon UV exposure of the corresponding PAGs.

For this purpose it is crucial to understand and to appreciate the microscopic mechanisms that cause PAGs with the fluorine free PAGs as taught herein to generate upon UV exposure fluorine free acids that have a high acid dissociation constant. For this, it is instructive to consider exemplary disulfonic acids generated upon UV exposure of the respective PAGs, based on the aromatic elements dihydroanthracene, biphenylene, and naphthalene, as depicted in FIG. 5. FIG. 5 depicts disulfonic acids generated upon UV exposure of the corresponding PAGs based on the aromatic elements dihydroanthracene, biphenylene, and naphthalene, wherein the generated disulfonic acids comprise: 5,10-dihydroanthracene (501), biphenylene (502), naphthalene (503), 5,10-dihydroanthracene-1,9-disulfonic acid (504), biphenylene-1,8-disulfonic acid (505), naphthalene-1,8-disulfonic acid (506), 5,10-dihydroanthracene-1,6-disulfonic acid (507), biphenylene-1,5-disulfonic acid (508), and naphthalene-1,5-disulfonic acid (509).

Ab initio gas phase simulation, which is a computational chemistry method based on quantum chemistry, of proton dissociation at the Perdew-Burke-Esnzerof and double-zeta valence polarizations (PBE/DZVP) level of theory was performed. The proton dissociation energy of the acids depicted in FIG. 5 is: (504) 267 kcal/mol, (505) 274 kcal/mol, (506) 275 kcal/mol, (507) 277 kcal/mol, (508) 275 kcal/mol, and (509) 274 kcal/mol.

The lower the proton dissociation energy, the more labile the proton, i.e., the "stronger" the acid. For comparison, the proton dissociation energy of the trifluoromethanesulfonic acid, depicted in FIG. 1, is 267 kcal/mol, and the proton dissociation energy of p-toluenesulfonic acid and camphorsulfonic acid, depicted in FIG. 3, is 284 kcal/mol for both.

Surprisingly, it was observed that 5,10-dihydroanthracene-1,9-disulfonic acid (504) comprising as central cycle a cyclohexane cycle has a proton dissociation energy (267 kcal/mol) similar to that of trifluoromethanesulfonic acid (267 kcal/mol), i.e., its acid dissociation constant is similar to that of trifluoromethanesulfonic acid.

Furthermore, it could be noted that there is a geometrical arrangement optimum for the two sulfonic acid groups to yield acids with this low proton dissociation energy. The proton dissociation energy is higher (about 275 kcal/mol) for biphenylene-1,8-disulfonic acid (505) comprising as central cycle a cyclobutane cycle and naphthalene-1,8-disulfonic acid (506) comprising no central cycle, since both disulfonic acids have two sulfonic acid groups that are in too close proximity.

The proton dissociation energy is also higher for 5,10-dihydroanthracene-1,6-disulfonic acid (507), biphenylene-1,5-disulfonic acid (508), and naphthalene-1,5-disulfonic acid (509), all three disulfonic acids with two sulfonic acid groups on different sides of the plane of planer of the condensed ring system that are too far from each other, that their orbitals can interact with each other.

Figure 6:
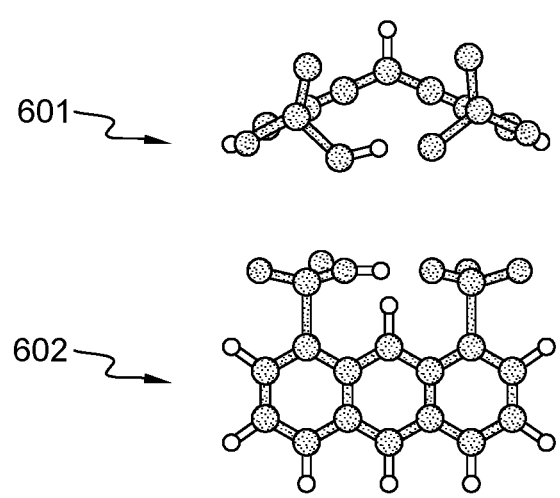
FIG. 6 shows the top view and front view of molecular structure of 5,10-dihydroanthracene-1,9-disulfonic acid after proton dissociation: 601 top view, and 602 front view.

FIG. 6 displays the top view 601 and front view 602 of the molecular structure of 5,10-dihydroanthracene-1,9-disulfonic acid (504) after proton dissociation as obtained by ab initio simulation. The remaining proton is stabilized by the bending of the cyclohexane central cycle of the 5,10-dihydroanthracene element. This steric effect is complemented by the electronic effect of the negatively charged sulfonate group. The ability to stabilize the conjugate acid through said structural modification and said electronic effect is the microscopic origin of 5,10-dihydroanthracene-1,9-disulfonic acid's low proton dissociation energy, which is a measure of the relative stability of the acid and its conjugate.

Figure 7A:
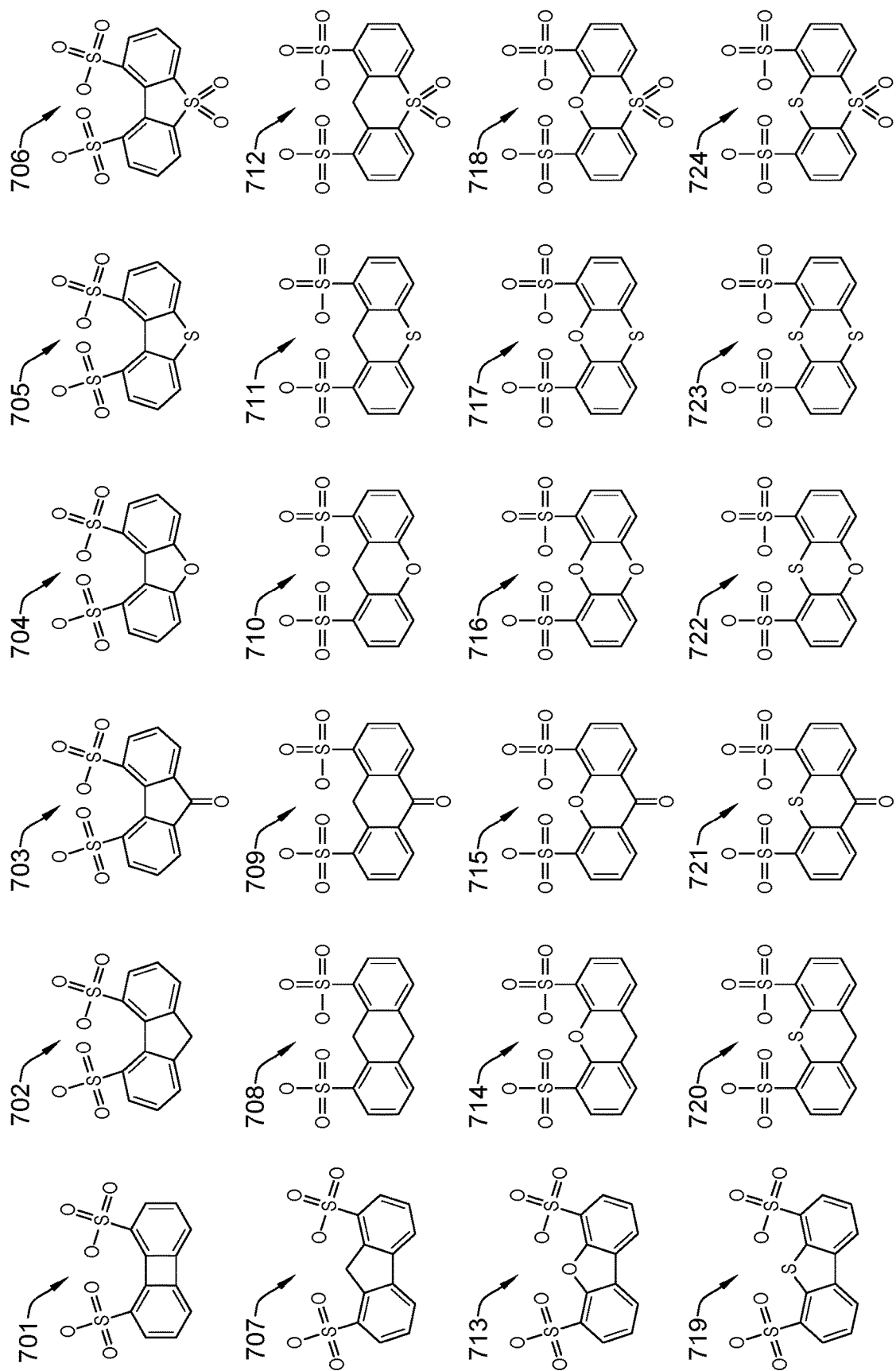
FIG. 7A illustrates examples of PAG anions according to an embodiment of the present invention.

Embodiments of the PAG anions according to the present invention comprising a first sulfonate group bonded to the first benzene moiety and a second sulfonate group bonded to the second benzene moiety as defined herein are displayed in FIG. 7A. FIG. 7A illustrates examples of PAG anions according to the present invention, wherein examples of PAG anions comprise: biphenylene-1,8-disulfonate (701), fluorene-4,5-disulfonate (702), fluorenone-4,5-disulfonate (703), dibenzofuran-4,5-disulfonate (704), dibenzothiophene-4,5-disulfonate (705), 10,10-dioxodibenzothiophene-4,5-disulfonate (706), fluorene-1,9-disulfonate (707), 5,10-dihydroanthracene-1,9-disulfonate (708), anthrone-4,6-disulfonate (709), xanthene-4,6-disulfonate (710), thioxanthene-4,6-disulfonate (711), 10,10-dioxothioxanthene-4,6-disulfonate (712), dibenzofuran-1,9-disulfonate (713), xanthene-1,9-disulfonate (714), xanthone-4,6-disulfonate (715), oxanthrene-1,9-disulfonate (716), phenoxathiin-4,6-disulfonate (717, 10,10-dioxophenoxathiine-4,6-disulfonate (718), dibenzothiophene-1,9-disulfonate (719), thioxanthene-1,9-disulfonate (720), thioxanthone-4,6-disulfonate (721), phenoxathiin-1,9-disulfonate (722), thianthrene-1,9-disulfonate (723), and 5,5-dioxothianthrene-1,9-disulfonate (724).

Figure 7B:
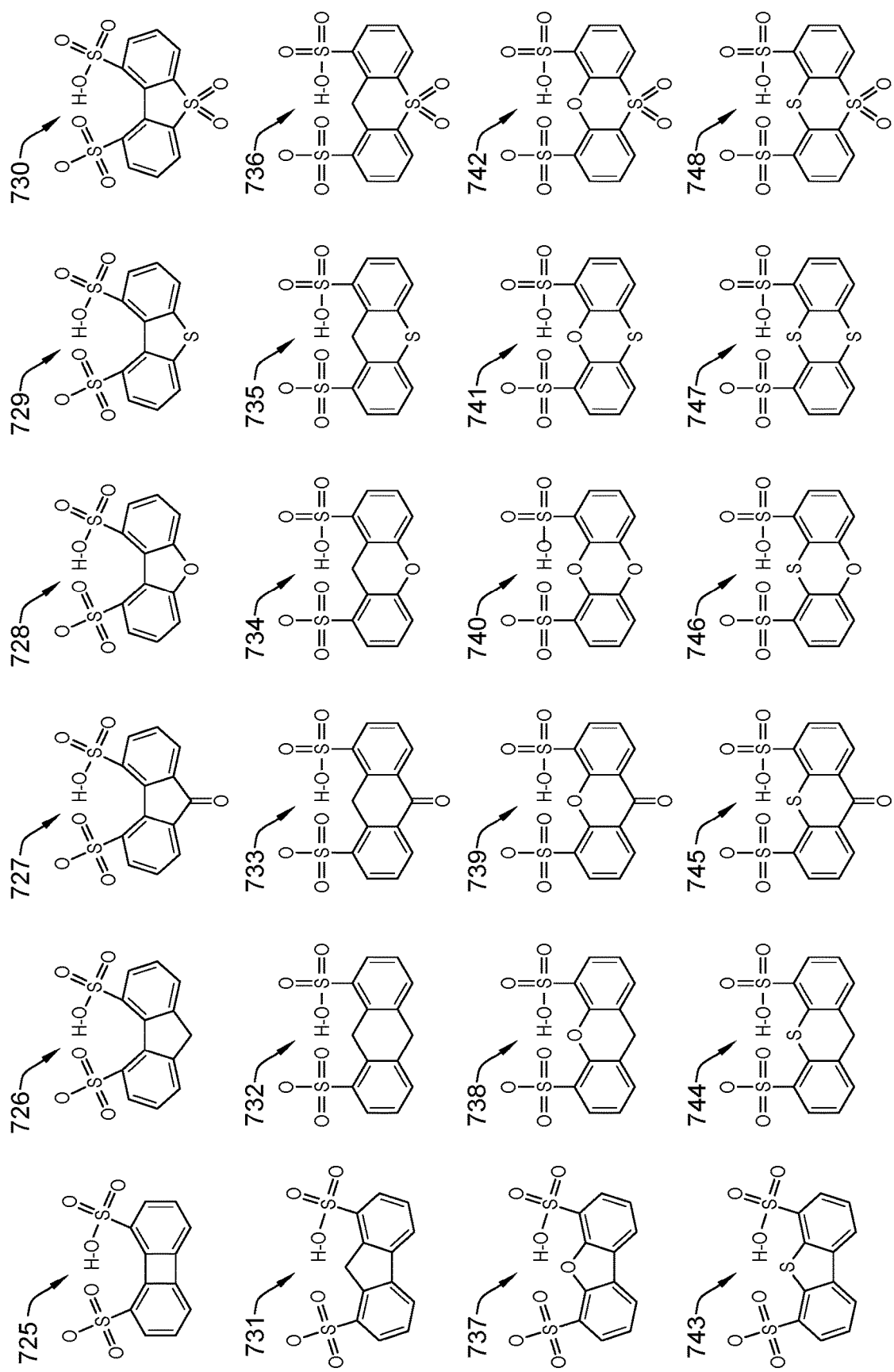
FIG. 7B illustrates examples of PAG anions according to an embodiment of the present invention.

Embodiments of the PAG anions according to the present invention comprising a sulfonate group bonded to the first benzene moiety and a sulfonic acid group bonded to the second benzene moiety or vice versa as defined herein are displayed in FIG. 7B. FIG. 7B depicts examples of PAG anions according to the present invention, wherein examples of PAG anions comprise: 1-sulfo-biphenylene-8-sulfonate (725), 4-sulfo-fluorene-5-sulfonate (726), 4-sulfo-fluorenone-5-sulfonate (727), 4-sulfo-dibenzofuran-5-sulfonate (728), 4-sulfo-dibenzothiophene-5-sulfonate (729), 4-sulfo-10,10-dioxodibenzothiophene-5-sulfonate (730), 1-sulfo-fluorene-9-sulfonate (731), 1-sulfo-5,10-dihydroanthracene-9-sulfonate (732), 4-sulfo-anthrone-6-sulfonate (733), 4-sulfo-xanthene-6-sulfonate (734), 4-sulfo-thioxanthene-6-sulfonate (735), 4-sulfo-10,10-dioxothioxanthene-6-sulfonate (736), 1-sulfo-dibenzofuran-9-sulfonate (737), 1-sulfo-xanthene-9-sulfonate (738), 4-sulfo-xanthone-6-sulfonate (739), 1-sulfo-oxanthrene-9-sulfonate (740), 4-sulfo-phenoxathiin-6-sulfonate, (741), 4-sulfo-10,10-dioxophenoxathiine-6-sulfonate (742), 1-sulfo-dibenzothiophene-9-sulfonate (743), 1-sulfo-thioxanthene-9-sulfonate (744), 4-sulfo-thioxanthone-6-sulfonate (745), 1-sulfo-phenoxathiin-9-sulfonate (746), 1-sulfo-thianthrene-9-sulfonate (747), and 1-sulfo-5,5-dioxothianthrene-9-sulfonate (748).

Figure 8:
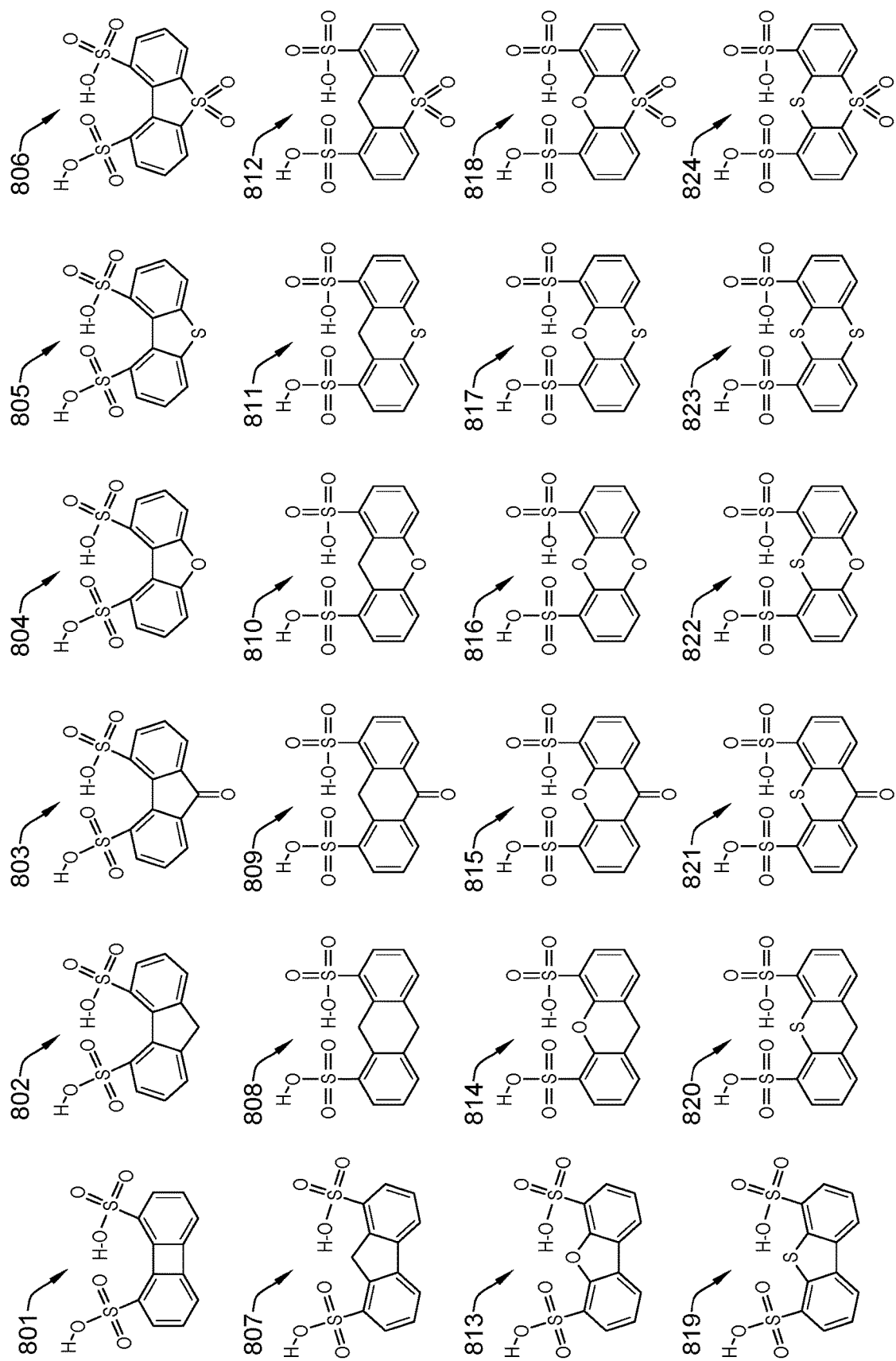
FIG. 8 shows disulfonic acids generated upon UV exposure by PAGs comprising PAG anions according to the present invention.

FIG. 8 displays the corresponding disulfonic acids that are generated upon UV exposure of the PAGs comprising the PAG anions described before, wherein the disulfonic acids generated upon UV exposure by PAGs comprising PAG anions according to the present invention and shown in FIGS. 7A and 7B comprise: biphenylene-1,8-disulfonic acid (801), fluorene-4,5-disulfonic acid (802), fluorenone-4,5-disulfonic acid (803), dibenzofuran-4,5-disulfonic acid (804), dibenzothiophene-4,5-disulfonic acid (805), 10,10-dioxodibenzothiophene-4,5-disulfonic acid (806), (fluorene-1,9-disulfonic acid (807), 5,10-dihydroanthracene-1,9-disulfonic acid (808), anthrone-4,6-disulfonic acid (809), xanthene-4,6-disulfonic acid (810), thioxanthene-4,6-disulfonic acid (811), 10,10-dioxothioxanthene-4,6-disulfonic acid (812), dibenzofuran-1,9-disulfonic acid (813), xanthene-1,9-disulfonic acid (814), xanthone-4,6-disulfonic acid (815), oxanthrene-1,9-disulfonic acid (816), 21henoxathiine-4,6-disulfonic acid (817), 10,10-dioxophenoxathiine-4,6-disulfonic acid (818), dibenzothiophene-1,9-disulfonic acid (819), thioxanthene-1,9-disulfonic acid (820), thioxanthone-4,6-disulfonic acid (821), 21henoxathiine-1,9-disulfonic acid (822), thianthrene-1,9-disulfonic acid (823), and 5,5-dioxothianthrene-1,9-disulfonic acid (824). The photoreaction of a PAG comprising PAG anions depicted in FIGS. 7A and 7B is analogous to the photoreaction shown in FIGS. 14A and 14B, respectively.

Surprisingly, the disulfonic acids obtained upon UV exposure of the PAGs comprising the PAG anions according to the present invention are characterized in that they have good acidity properties, i.e., they have a low proton dissociation energy and concomitantly a high acid dissociation constant.

Ab initio gas phase simulation of proton dissociation at the PBE/DZVP level of theory was performed. The proton dissociation energy of the disulfonic acids depicted in FIG. 8 is: 275 kcal/mol for (801), 274 kcal/mol for (802), 266 kcal/mol for (803), 273 kcal/mol for (804), 272 kcal/mol for (805), 262 kcal/mol for (806), 275 kcal/mol for (807), 267 kcal/mol for (808), 262 kcal/mol for (809), 263 kcal/mol for (810), 264 kcal/mol for (811), 252 kcal/mol for (812), 273 kcal/mol for (813), 278 kcal/mol for (814), 269 kcal/mol for (815), 271 kcal/mol for (816), 276 kcal/mol for (817), 268 kcal/mol for (818), 273 kcal/mol for (819), 265 kcal/mol for (820), 268 kcal/mol for (821), 270 kcal/mol for (822), 266 kcal/mol for (823), and 258 kcal/mol for (824).

For example, PAGs that comprise the anions 5,10-dihydroanthracene-1,9-disulfonate (708) and 1-sulfo-5,10-dihydroanthracene-9-sulfonate, comprising a six-membered central cycle (732) generate upon UV exposure acids that have a proton dissociation energy (267 kcal/mol) similar to that of trifluoromethanesulfonic acid (267 kcal/mol), i.e., their acid dissociation constant is similar to that of trifluoromethanesulfonic acid. And also, for example, PAGs that comprise the anions thianthrene-1,9-disulfonate (723) and 1-sulfo-thianthrene-9-sulfonate (747) comprising a six-membered central cycle with two S heteroatoms generate upon UV exposure acids that have a proton dissociation energy (266 kcal/mol) similar to that of trifluoromethanesulfonic acid (267 kcal/mol), i.e., their acid dissociation constant is similar to that of trifluoromethanesulfonic acid.

Hence, with the PAGs that comprise the PAG anions according to the present invention, disulfonic acids that have an acid dissociation constant similar to that of trifluoromethanesulfonic acid, which is a reference benchmark, can be obtained.

Beyond that, it was observed, that the proton dissociation energy of the acid that is generated upon UV exposure can be systematically tuned by modifying the size of the PAG anions' central cycle and/or by functionalizing the PAG anions' central cycle, for example, by a carbonyl, sulfinyl, or sulfonyl group (see, for example, FIGS. 7A and 7B). Steric effects and electronic effects may advantageously be used to devise PAGs that comprise fluorine free anions and that generate upon UV exposure fluorine free acids have an acid dissociation constant similar to or even larger than that of trifluoromethanesulfonic acid.

For example, PAGs that comprise the anions 10,10-dioxothioxanthene-4,6-disulfonate (712) and 4-sulfo-10,10-dioxothioxanthene-6-sulfonate (736) comprising a six-membered central cycle with a functionalizing sulfonyl group, where the steric effect is complemented by the electronic effect of an electron-withdrawing sulfonyl group in the cyclohexane central cycle, generate upon UV exposure acids that have a proton dissociation energy (252 kcal/mol) substantially smaller than that of trifluoromethanesulfonic acid (267 kcal/mol), i.e., their acid dissociation constant is substantially larger than that of trifluoromethanesulfonic acid. And also, for example, PAGs that comprise the anions 5,5-dioxothianthrene-1,9-disulfonate (724) and 1-sulfo-5,5-dioxothianthrene-9-sulfonate (748) comprising a six-membered central cycle with a S heteroatom and a functionalizing sulfonyl group, where the steric effect is complemented by the electronic effect of an electron-withdrawing sulfonyl group in the cyclohexane central cycle, generate upon UV exposure acids that have a proton dissociation energy (258 kcal/mol) substantially smaller than that of trifluoromethanesulfonic acid (267 kcal/mol), i.e., their acid dissociation constant is substantially larger than that of trifluoromethanesulfonic acid.

The proton dissociation energy of the PAG anions 1-sulfo-5,10-dihydroanthracene-9-sulfonate (732) and 4-sulfo-10,10-dioxothioxanthene-6-sulfonate (736)) is 318 kcal/mol and 312 kcal/mol, respectively. In UV-unexposed regions the acid-labile protection group of the acid-labile polymer will not be removed by these PAG anions and the further "sulfo-sulfonate"-type PAG anions taught here. For contextual reference only, the proton dissociation energy of acetic acid is 312 kcal/mol. The acid dissociation constant of acetic acid is about 20 orders of magnitude smaller than that of trifluoromethanesulfonic acid (and about 6 orders of magnitude smaller than that of p-toluenesulfonic acid and camphorsulfonic acid).

In an embodiment of the present invention, the polycyclic aromatic photoacid generator compound anion comprises an electron withdrawing group substituent at the first and/or second benzene moiety. An electron withdrawing group is a group that draws electron density from neighboring atoms towards itself, usually by resonance of inductive effects. In the present case, the electron withdrawing group draws electron from the benzene moiety to which the electron withdrawing group is chemically bonded.

The electron withdrawing group is selected from the group consisting of fluoro, perfluoroalkyl, alkylsulfinyl, alkylsulfonyl, nitro, and cyano. In one particular embodiment, the electron withdrawing group is selected form the group consisting of nitro and cyano.

In one particular embodiment of the polycyclic aromatic photoacid generator compound anion according to the present invention, either the first benzene moiety can be substituted with an electron withdrawing group or the second benzene moiety can be substituted with an electron withdrawing group or both the first and the second benzene moiety can be substituted with an electron withdrawing group. If both benzene moieties are substituted, the electron withdrawing group substituents can be identical or different. In one particular embodiment, both benzene moieties are substituted with identical electron withdrawing groups.

The electron withdrawing group substituent is in a first alternative in ortho or para position to the first sulfonate group and the second sulfonate group of the first and second benzene moiety. In a second alternative, the electron withdrawing group substituent is in ortho or para position to the sulfonate group and the sulfonic acid group of the first and second benzene moiety.

Figure 9A:
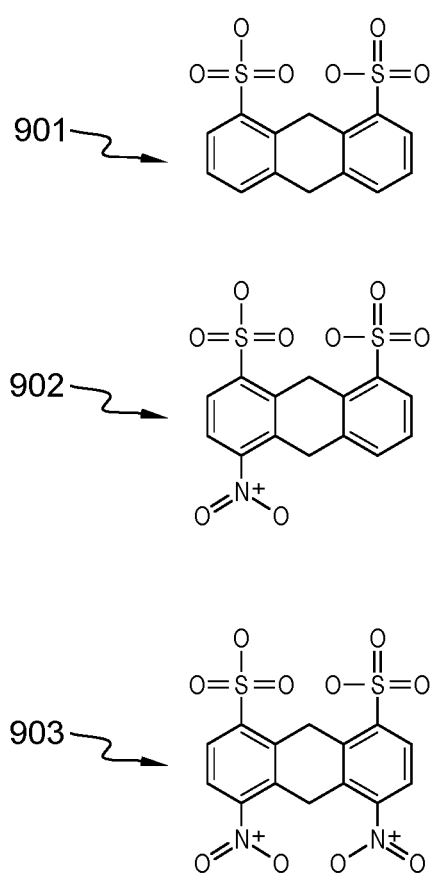
FIG. 9A shows examples of substituted PAG anions according to an embodiment of the present invention.
Figure 9B:
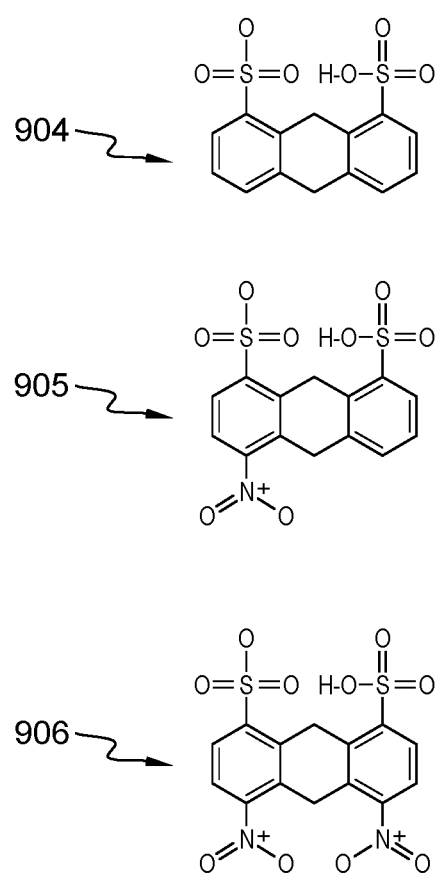
FIG. 9B shows examples of substituted PAG anions according to an embodiment of the present invention.

Exemplary PAG anions according to the present invention comprising electron withdrawing nitro group substituents at the first benzene moiety and/or the second benzene moiety are depicted in FIGS. 9A and 9B. FIG. 9A shows examples of substituted PAG anions according to embodiments of the present invention, wherein the substituted PAG anions comprise: 5,10-dihydroanthracene-1 (901), 9-disulfonate, 4-nitro-5,10-dihydroanthracene-1,9-disulfonate (902), and 4,6-dinitro-5,10-dihydroanthracene-1,9-disulfonate (903). As shown in FIG. 9A the PAG anions wherein a first sulfonate group is chemically bonded to the first benzene moiety and a second sulfonate group is chemically bonded to the second benzene moiety comprises (i) an electron withdrawing nitro group chemically bonded to the first benzene moiety, and (ii) two electron withdrawing nitro groups chemically bonded to the first and second benzene moiety.

FIG. 9B illustrates examples of substituted PAG anions according to embodiments of the present invention, wherein examples of substituted PAG anions comprise: 1-sulfo-5,10-dihydroanthracene-9-sulfonate (904), 1-sulfo-4-nitro-5,10-dihydroanthracene-9-sulfonate (905), and 1-sulfo-4,6-dinitro-5,10-dihydroanthracene-9-sulfonate (906). As shown in FIG. 9B the PAG anions wherein a sulfonate group is chemically bonded to the first benzene moiety and a sulfonic acid group is chemically bonded to the second benzene moiety comprises (i) an electron withdrawing nitro group chemically bonded to the first benzene moiety, and (ii) two electron withdrawing nitro groups chemically bonded to the first and second benzene moiety.

Figure 10:
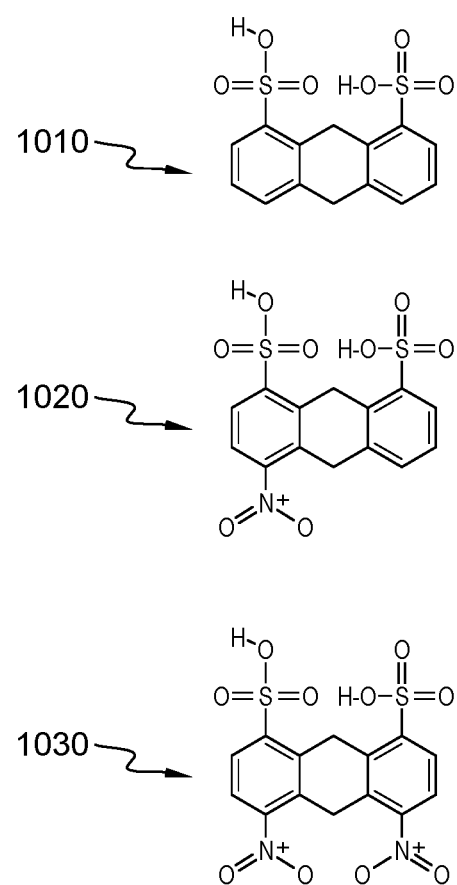
FIG. 10 shows disulfonic acids generated upon UV exposure by PAGs comprising PAG anions according to an embodiment of this invention and shown in FIGS. 9A and 9B.

The corresponding acids generated upon UV exposure of the PAGs comprising the polycyclic aromatic photoacid generator compound anions according to the present invention and depicted in FIGS. 9A and 9B are shown in FIG. 10. FIG. 10 shows disulfonic acids generated upon UV exposure by PAGs comprising PAG anions according to an embodiment of this invention and shown in FIGS. 9A and 9B, wherein the disulfonic acids generated upon UV exposure by PAGs comprising PAG anions comprise: 5,10-dihydroanthracene-1,9-disulfonic acid (1010), 4-nitro-5,10-dihydroanthracene-1,9-disulfonic acid (1020), and 4,6-dinitro-5,10-dihydroanthracene-1,9-disulfonic acid (1030).

Ab initio gas phase simulation of proton dissociation at the PBE/DZVP level of theory was performed. The proton dissociation energy of the acids depicted in FIG. 10 is: 267 kcal/mol for (1010), 255 kcal/mol for (1020), and 251 kcal/mol for (1030).

It could be observed, that the proton dissociation energy of the acid that is generated upon UV exposure can be systematically tuned by substituting the first and/or the second benzene moiety of the polycyclic aromatic photoacid generator compound anion of formula (I) with an electron withdrawing group. The steric effect is complemented by the electronic effect of the electron withdrawing group at the first and/or second benzene moieties. By substituting the first and/or the second benzene moiety of the polycyclic aromatic photoacid generator compound anion of formula (I) with an electron withdrawing group, the proton dissociation energy of the acid that is generated upon UV exposure can be systematically reduced, i.e., the acid dissociation constant of the acid that is generated upon UV exposure can be systematically increased.

The PAGs that comprise the polycyclic aromatic photoacid generator compound anions 5,10-dihydroanthracene-1,9-disulfonate (901) and 1-sulfo-5,10-dihydroanthracene- 9-sulfonate (904) generate upon UV exposure disulfonic acids that have a proton dissociation energy (267 kcal/mol) similar to that of trifluoromethanesulfonic acid (267 kcal/mol), i.e., their acid dissociation constant is similar to that of trifluoromethanesulfonic acid.

The corresponding disubstituted PAGs that comprise the anions 4,6-dinitro-5,10-dihydroanthracene-1,9-disulfonate (903) and 4,6-dinitro-1-sulfo-5,10-dihydroanthracene-9-sulfonate (906), where the steric effect is complemented by the electronic effect of an electron-withdrawing nitro group substituent added each to the benzene moieties, generate upon UV exposure acids that have a proton dissociation energy (251 kcal/mol) substantially smaller than that of trifluoromethanesulfonic acid (267 kcal/mol), i.e., their acid dissociation constant is substantially larger than that of trifluoromethanesulfonic acid.

It could be further observed, that adding electron-withdrawing nitro group substituents to the PAG anions' benzene moieties or functionalizing the PAG anions' cyclohexane central cycle with an electron-withdrawing sulfonyl group have a similar influence on the proton dissociation energy. For example, PAGs that comprise the anions 4,6-dinitro-5, 10-dihydroanthracene-1,9-disulfonate (903) and 4,6-dinitro-1-sulfo-5,10-dihydroanthracene-9-sulfonate (906), where the steric effect is complemented by the electronic effect of an electron-withdrawing nitro group substituent added each to the benzene moieties, and PAGs that comprise the anions 10,10-dioxothioxanthene-4,6-disulfonate (712) and 4-sulfo-10,10-dioxothioxanthene-6-sulfonate (736), where the steric effect is complemented by the electronic effect of an electron-withdrawing sulfonyl group in the cyclohexane central cycle, generate upon UV exposure acids that have a similar proton dissociation energy of 251 to 252 kcal/mol.

In order to devise photoacid generators that can be used to increase the sensitivity of chemically amplified photoresists for EUV lithography, it is crucial to understand and to appreciate the microscopic mechanisms that cause photon absorption events and that cause photoacid generator decomposition in the EUV, in contrast to in the DUV.

The DUV (193 nm or 248 nm, 6 eV or 5 eV, respectively) photon absorption is determined by the molecular orbitals of the photoresist material. The absorbed photons can directly and selectively cause resonant electronic transition in the photoacid generator, resulting in the generation of an acid. The sensitivity of chemically amplified photoresists for DUV lithography can be increased by adjusting the molecular structure of the photoacid generator.

By contrast, the EUV (13.5 nm, 92 eV, soft X-ray) photon absorption is determined by the atomic composition of the photoresist material, i.e., the molecular structure is essentially not relevant.

Embodiments of the present invention test the photon absorption cross-section pa at 92 eV of known naturally occurring elements. The absorption of photons in a layer of thickness d is given by $1-\exp(-n \mu_a d)$, where n is the number of atoms per unit volume in the layer.

DUV photoresist platforms are mainly composed of light elements such as H, C, O, F, and S, which all have for 92 eV photons a low absorption cross section. This limits their EUV performance.

In order to increase the chemically amplified photoresists' 92-eV-photon absorption cross-section, elements that have a large absorption cross-section at this photon energy must be added to the photoresist composition, resulting in an increased sensitivity of the chemically amplified photoresist composition for EUV lithography.

In order to advantageously increase the 92 eV absorption in the chemically amplified photoresist, the element for a photoacid generator compound anion substituent must have an absorption cross section for 92 eV photons of at least $0.5 \times 10^7 \cdot cm^2/mol$. In one particular embodiment of the present invention, the element for a photoacid generator compound anion substituent must have an absorption cross section for 92 eV photons of at least $0.75 \times 10^7 \cdot cm^2/mol$. In a particular embodiment of the present invention, the element for a photoacid generator compound anion substituent must have an absorption cross section for 92 eV photons of at least $1.0 \times 10^7 \cdot cm^2/mol$.

The elements directly incorporated into the polycyclic aromatic photoacid generator compound anion according to the present invention and having the above specified absorption cross section for 92 eV photons result in a better sensitivity of chemically amplified photoresists for EUV lithography.

The elements having an absorption cross section for 92 eV photons of at least $0.5 \times 10^7 \cdot cm^2/mol$ are selected from the group consisting of the elements In, Sn, Sb, Te, Tl, Pb, and Bi.

In some embodiments of the present invention, the elements having an absorption cross section for 92 eV photons of at least $0.75 \times 10^7 \cdot cm^2/mol$ are selected from the group consisting of In, Sn, Sb, Te, Pb, and Bi.

In one particular embodiment of the present invention, the elements having an absorption cross section for 92 eV photons of at least $1.0 \times 10^7 \cdot cm^2/mol$ are selected from the group consisting of In, Sn, Sb, Te, and Bi.

Additionally, the elements In, Sn, Sb, and Bi may be used under toxicity consideration since organometallic compounds comprising Te, Tl, and Pb are toxic.

Additionally, the elements Sn, Sb, and Bi may be used in comparison to the element In since organometallic compounds comprising In exhibit at room temperature less stable photoreactions. In various embodiments of the present invention, Sb and Bi are used because organoantimony and organobismuth compounds have a toxicity advantage over organotin compounds. Moreover, bismuth compounds have a cost advantage.

In an embodiment of the present invention, the polycyclic aromatic photoacid generator compound anion according to the present invention, the central cycle comprises an element having for 92 eV photons an absorption cross section of at least $0.5 \times 10^7 \cdot cm^2/mol$.

In some embodiments of the present invention, the polycyclic aromatic photoacid generator compound anion according to the present invention is characterized in that the first and/or second benzene moiety is instead of the electron withdrawing group as described herein substituted with a group comprising an element having for 92 eV photons an absorption cross section of at least $0.5 \times 10^7 \cdot cm^2/mol$ (in the following referred to as "element group substituent").

In another embodiment of the present invention, the polycyclic aromatic photoacid generator compound anion according to the present invention is characterized in that the central cycle comprises an element having for 92 eV photons an absorption cross section of at least $0.5 \times 10^7 \cdot cm^2/mol$ and the first and/or second benzene moiety is substituted with a group comprising an element having for 92 eV photons an absorption cross section of at least $0.5 \times 10^7 \cdot cm^2/mol$.

In an alternative variant, the first and/or second benzene moiety is in addition to the electron withdrawing group as described herein further substituted with a group comprising an element having for 92 eV photons an absorption cross section of at least $0.5 \times 10^7 \cdot cm^2/mol$ (in the following also referred to as "element group substituent").

In an embodiment of the present invention, both, the first and second benzene moieties of the polycyclic aromatic photoacid generator compound anion are (further) substituted with a group comprising an element having for 92 eV photons an absorption cross section of at least $0.5 \times 10^7 \cdot cm^2/mol$. The photoacid generator compound' 92 eV absorption scales with the number of absorbing elements. Thus, the substitution with element group substituents on both, the first and second benzene moieties of the polycyclic aromatic photoacid generator compound anion will result in about twice as many 92-eV-photons being absorbed as for a substitution with only one element group on either the first or second benzene moiety.

In one particular embodiment of the present invention, the element having for 92 eV photons an absorption cross section of at least $0.5 \times 10^7 \cdot cm^2/mol$ is selected from the group consisting of In, Sn, Sb, Te, Tl, Pb, and Bi.

In a particular embodiment of the present invention, the element having for 92 eV photons an absorption cross section of at least $0.5 \times 10^7 \cdot cm^2/mol$ is selected from the group consisting of Sn, Sb, and Bi.

The "element group substituent" is a substituent selected from the group consisting of trialkylstannyl, dialkylantimonyl, tetraalkylantimonyl, dialkylbismuthyl, tetraalkylbismuthyl, triarylstannyl, diarylantimonyl, tetraarylantimonyl, diarylbismuthyl, and tetraarylbismuthyl. In one particular embodiment, the "element group substituent" is a substituent selected from the group consisting of trialkylstannyl, dialkylantimonyl, dialkylbismuthyl, triarylstannyl, diarylantimonyl, and diarylbismuthyl.

The alkyl group in the "element group substituent" may be a linear or branched or a cyclic unsubstituted or substituted alkyl group having 1 to 10 carbon atoms; or derivatives thereof. The aryl group in the "element group substituent" is an unsubstituted or substituted aryl group having 6 to 18 carbon atoms; or derivatives thereof. Instead of the alkyl or aryl group as described before, the "element group substituent" can comprise an unsubstituted or substituted unsaturated or saturated heterocyclic group having a 5 to 18 membered ring and having one or two heteroatoms; or derivatives thereof.

In one embodiment, the linear or branched alkyl group is selected from the group consisting of methyl, ethyl, propyl, butyl, pentyl, hexyl, heptyl, octyl, nonyl, decyl and derivatives thereof, and/or the cyclic alkyl group is selected from the group consisting of cyclopentane, cyclohexane, cycloheptane, cyclooctane and derivatives thereof, and/or the aryl group is selected from the group consisting of phenyl, naphthyl, anthracenyl, phenanthrenyl and derivatives thereof; and/or the saturated or unsaturated heterocyclic group having one or two heteroatoms is selected from the group consisting of pyrrolidine, pyrrole, tetrahydrofuran, furan, tetrahydrothiophene, thiophene, imidazolidine, imidazole, oxazolidine, oxyzole, thiazolidine, thiazole, dioxolane, dithiolane, piperidine, pyridine, tetrahydropyran, pyran, thiane, thiopyran, diazinane, diazine, in particular pyridazin (1,2-diazin), pyrimidine (1,3-diazin), pyrazin (1,4-diazin), morpholine, oxazine, thiomorpholine, thiazine, dioxane, dioxine, dithiane, dithiin, quinolone, isoquinoline and derivatives thereof.

In one particular embodiment, the alkyl group or the aryl group or the heterocyclic group is/are optionally substituted. The phrase "optionally substituted" is used interchangeably with the phrase "substituted or unsubstituted." As described herein, the alkyl, aryl or heterocyclic group of the "element group substituent" can optionally be substituted with one or more substituents. In one particular embodiment, the alkyl group or the aryl group or the heterocyclic group, include(s) at least one substituent selected from the group consisting of halogen, hydroxyl, alkyl, alkoxy, aryl, aryloxy, nitro, and cyano.

Due to their delocalized electrons, aryl groups or aromatic cycles and unsaturated heterocyclic groups, are more stable and, thus the "element group substituents" triarylstannyl, diarylantimonyl, and diarylbismuthyl may be used, compared for example to the "element group substituents" trialkylstannyl, dialkylantimonyl, and dialkylbismuthyl.

The element group substituent is in a first alternative in ortho or para position to the first sulfonate group and the second sulfonate group of the first and second benzene moiety. In a second alternative, the element group substituent is in ortho or para position to the sulfonate group and the sulfonic acid group of the first and second benzene moiety.

If the PAG anion comprises an electron withdrawing substituent and a group comprising an element having for 92 eV photons an absorption cross section of at least $0.5 \times 10^7 \cdot cm^2/mol$ substituent both substituents are arranged in ortho- and para-position to the first sulfonate group and the second sulfonate group of the first and/or second benzene moiety, or in ortho- and para-position to the sulfonate group and the sulfonic acid group of the first and/or second benzene moiety.

Figure 11A:
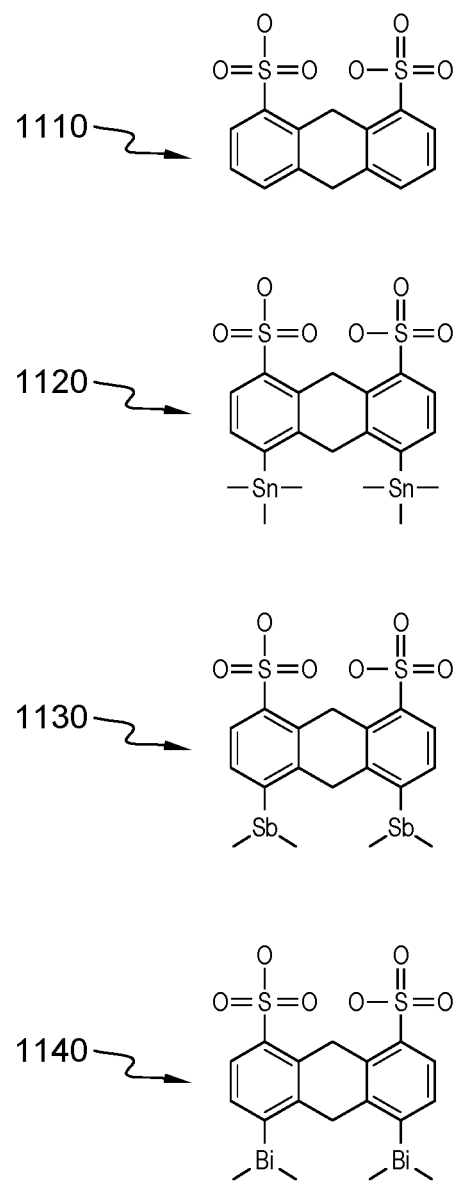
FIG. 11A shows examples of substituted PAG anions according to an embodiment of the present invention.
Figure 11B:
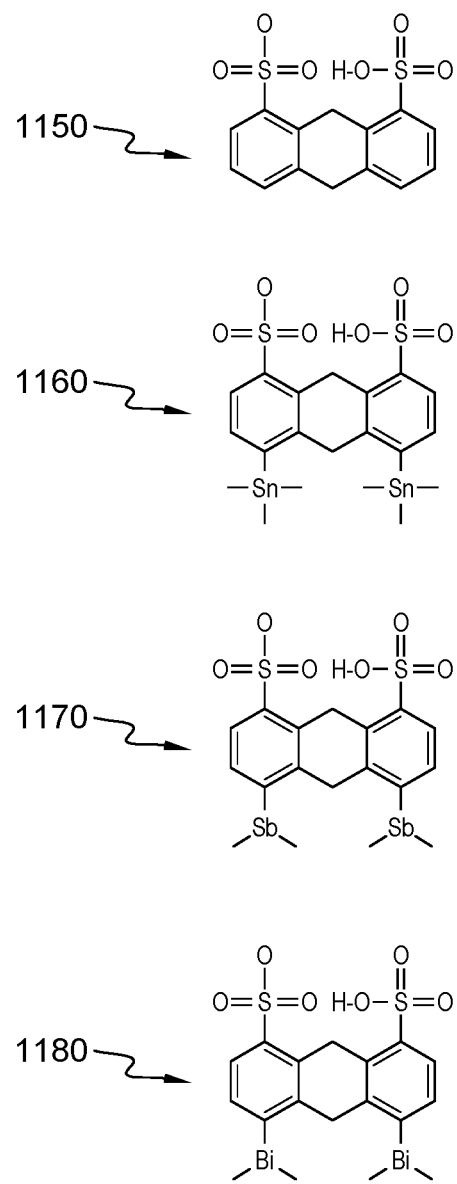
FIG. 11B shows examples of substituted PAG anions according to embodiments of the present invention.

Exemplary embodiments of PAG anions comprising an element having for 92 eV photons an absorptions cross section of at least $0.5 \times 10^7 \cdot cm^2/mol$ according to the present invention, and especially suited for EUV lithography, are displayed in FIGS. 11A and 11B. The PAG anions comprise stannyl, antimonyl, and bismuthyl group substituents at the first and second benzene moieties. FIG. 11A shows examples of substituted PAG anions according to an embodiment of the present invention, wherein examples of substituted PAG anions comprise: 5,10-dihydroanthracene-1,9-disulfonate (1110), 4,6-bis(trimethylstannyl)-5,10-dihydroanthracene-1,9-disulfonate (1120), 4,6-bis(dimethylantimonyl)-5,10-dihydroanthracene-1,9-disulfonate (1130), and 4,6-bis(dimethylbismuthyl)-5,10-dihydroanthracene-1,9-disulfonate (1140). FIG. 11B shows examples of substituted PAG anions according to an embodiment the present invention, wherein examples of substituted PAG anions comprise: 1-sulfo-5,10-dihydroanthracene-9-sulfonate (1150), 1-sulfo-4,6-bis(trimethylstannyl)-5,10-dihydroanthracene-9-sulfonate (1160), 1-sulfo-4,6-bis(dimethylantimonyl)-5,10-dihydroanthracene-9-sulfonate (1170), and 1-sulfo-4,6-bis(dimethylbismuthyl)-5,10-dihydroanthracene-9-sulfonate (1180).

Figure 12:
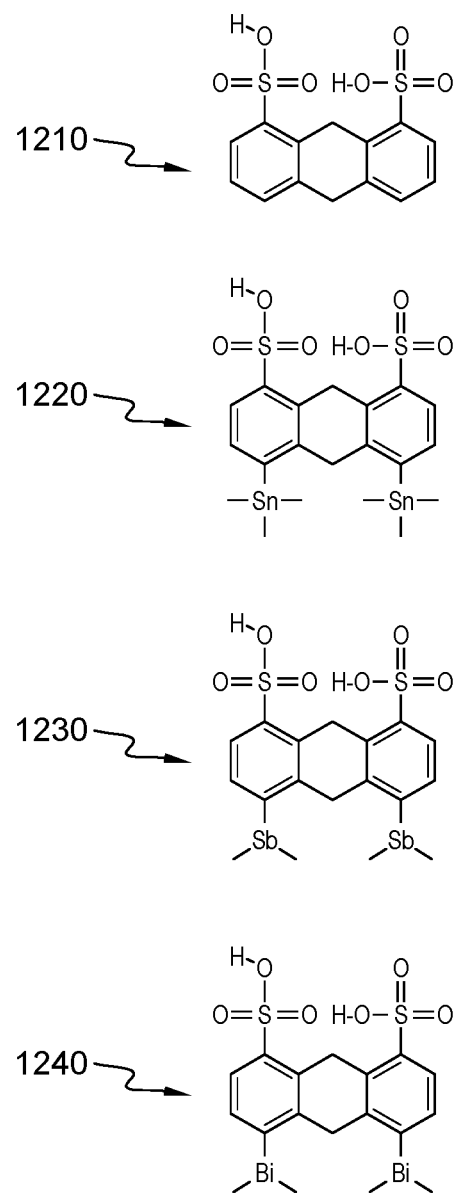
FIG. 12 depicts disulfonic acids generated upon UV exposure by PAGs comprising PAG anions according to embodiments of the present invention and shown in FIGS. 11A and 11B.

FIG. 12 displays the corresponding acids generated upon UV exposure by PAGs comprising the PAG anions according to embodiments of the present invention as shown in FIGS. 11A and 11B. FIG. 12 illustrates disulfonic acids generated upon UV exposure by PAGs comprising PAG anions according to the present invention and shown in FIGS. 11A and 11B, wherein disulfonic acids generated upon UV exposure by PAGs comprising PAG anions comprise: 5,10-dihydroanthracene-1,9-disulfonic acid (1210), 4,6-bis(trimethylstannyl)-5,10-dihydroanthracene-1,9-disulfonic acid (1220), 4,6-bis(dimethylantimonyl)-5,10-dihydroanthracene-1,9-disulfonic acid (1230), and 4,6-bis(dimethylbismuthyl)-5,10-dihydroanthracene-1,9-disulfonic acid (1240).

Ab initio gas phase simulation of proton dissociation at the PBE/DZVP level of theory was performed. The proton dissociation energy of the acids depicted in FIG. 12 is: 267 kcal/mol for (1210), 270 kcal/mol for (1220), 269 kcal/mol for (1230), and 267 kcal/mol for (1240).

It was observed that the proton dissociation energy of the acid that is generated upon UV exposure is essentially not influenced by adding stannyl, antimonyl, and bismuthyl-group substituents to the PAG anions benzene moieties (FIGS. 11A and 11B).

For example, PAGs that comprise the anions 4,6-bis (dimethylbismuthyl)-5,10-dihydroanthracene-1,9-disulfonate (1140) and 1-sulfo-4,6-bis(dimethylbismuthyl)-5,10-dihydroanthracene-9-sulfonate (1180), where bismuthyl group substituents are added to the benzene moieties, generate upon UV exposure acids that have a proton dissociation energy (267 kcal/mol) still similar to that of trifluoromethanesulfonic acid (267 kcal/mol), i.e., their acid dissociation constant is similar to that of trifluoromethanesulfonic acid.

In particular embodiments of the PAG anions according to the present invention comprising a first sulfonate group bonded to the first benzene moiety and a second sulfonate group bonded to the second benzene moiety as defined herein are selected from the group consisting of: biphenylene-1,8-disulfonate (701), fluorene-4,5-disulfonate (702), fluorenone-4,5-disulfonate (703), dibenzofuran-4,5-disulfonate (704), dibenzothiophene-4,5-disulfonate (705), 10,10-dioxodibenzothiophene-4,5-disulfonate (706), fluorene-1,9-disulfonate (707), 5,10-dihydroanthracene-1,9-disulfonate (708), anthrone-4,6-disulfonate (709), xanthene-4,6-disulfonate (710), thioxanthene-4,6-disulfonate (711), 10,10-dioxothioxanthene-4,6-disulfonate (712), dibenzofuran-1,9-disulfonate (713), xanthene-1,9-disulfonate (714), xanthone-4,6-disulfonate (715), oxanthrene-1,9-disulfonate (716), phenoxathiin-4,6-disulfonate (717, 10,10-dioxophenoxathiine-4,6-disulfonate (718), dibenzothiophene-1,9-disulfonate (719), thioxanthene-1,9-disulfonate (720), thioxanthone-4,6-disulfonate (721), phenoxathiin-1,9-disulfonate (722), thianthrene-1,9-disulfonate (723), and 5,5-dioxothianthrene-1,9-disulfonate (724), as shown in FIG. 7A.

In particular embodiments of the PAG anions according to the present invention comprising a sulfonate group bonded to the first benzene moiety and a sulfonic acid group bonded to the second benzene moiety or vice versa as defined herein are selected from the group consisting of: 1-sulfo-biphenylene-8-sulfonate (725), 4-sulfo-fluorene-5-sulfonate (726), 4-sulfo-fluorenone-5-sulfonate (727), 4-sulfo-dibenzofuran-5-sulfonate (728), 4-sulfo-dibenzothiophene-5-sulfonate (729), 4-sulfo-10,10-dioxodibenzothiophene-5-sulfonate (730), 1-sulfo-fluorene-9-sulfonate (731), 1-sulfo-5,10-dihydroanthracene-9-sulfonate (732), 4-sulfo-anthrone-6-sulfonate (733), 4-sulfo-xanthene-6-sulfonate (734), 4-sulfo-thioxanthene-6-sulfonate (735), 4-sulfo-10,10-dioxothioxanthene-6-sulfonate (736), 1-sulfo-dibenzofuran-9-sulfonate (737), 1-sulfo-xanthene-9-sulfonate (738), 4-sulfo-xanthone-6-sulfonate (739), 1-sulfo-oxanthrene-9-sulfonate (740), 4-sulfo-phenoxathiin-6-sulfonate, (741), 4-sulfo-10,10-dioxophenoxathiine-6-sulfonate (742), 1-sulfo-dibenzothiophene-9-sulfonate (743), 1-sulfo-thioxanthene-9-sulfonate (744), 4-sulfo-thioxanthone-6-sulfonate (745), 1-sulfo-phenoxathiin-9-sulfonate (746), 1-sulfo-thianthrene-9-sulfonate (747), and 1-sulfo-5,5-dioxothianthrene-9-sulfonate (748), as shown in FIG. 7B.

The polycyclic aromatic photoacid generator compound anions according to the present invention encompass in addition to the above specified polycyclic aromatic photoacid generator compound anions also derivatives, wherein the central cycle comprises the element having for 92 eV photons (EUV) an absorption cross section of at least $0.5 \times 10^7 \cdot cm^2/mol$ selected from the group consisting of tin, antimony, and bismuth; and/or wherein the element group substituent is on the first benzene moiety and/or second benzene moiety and is selected from the group consisting of stannyl group, antimonyl group, and bismuthyl group substituents; and/or wherein the electron withdrawing substituent is on the first benzene moiety and/or second benzene moiety and is selected from the group consisting of fluoro, perfluoroalkyl, alkylsulfinyl, alkylsulfonyl, nitro, cyano, as described before.

In an embodiment of the present invention, the polycyclic aromatic photoacid generator compounds anion according to the present invention are selected from the group consisting of:

4,5-dinitro-biphenylene-1,8-disulfonate,
1-sulfo-4,5-dinitro-biphenylene-8-sulfonate,
4,5-bis(trimethylstannyl)-biphenylene-1,8-disulfonate,
4,5-bis(dimethylantimonyl)-biphenylene-1,8-disulfonate,
4,5-bis(dimethylbismuthyl)-biphenylene-1,8-disulfonate,
1-sulfo-4,5-bis(trimethylstannyl)-biphenylene-8-sulfonate,
1-sulfo-4,5-bis(dimethylantimonyl)-biphenylene-8-sulfonate,
1-sulfo-4,5-bis(dimethylbismuthyl)-biphenylene-8-sulfonate,
1,8-dinitro-fluorene-4,5-disulfonate,
4-sulfo-1,9-dinitro-fluorene-5-sulfonate,
1,8-bis(trimethylstannyl)-fluorene-4,5-disulfonate,
1,8-bis(dimethylantimonyl)-fluorene-4,5-disulfonate,
1,8-bis(dimethylbismuthyl)-fluorene-4,5-disulfonate,
4-sulfo-1,8-bis(trimethylstannyl)-fluorene-5-sulfonate,
4-sulfo-1,8-bis(dimethylantimonyl)-fluorene-5-sulfonate,
4-sulfo-1,8-bis(dimethylbismuthyl)-fluorene-5-sulfonate,
1,8-dinitro-fluorenone-4,5-disulfonate,
4-sulfo-1,9-dinitro-fluorenone-5-sulfonate,
1,8-bis(trimethylstannyl)-fluorenone-4,5-disulfonate,
1,8-bis(dimethylantimonyl)-fluorenone-4,5-disulfonate,
1,8-bis(dimethylbismuthyl)-fluorenone-4,5-disulfonate,
4-sulfo-1,8-bis(trimethylstannyl)-fluorenone-5-sulfonate,
4-sulfo-1,8-bis(dimethylantimonyl)-fluorenone-5-sulfonate,
4-sulfo-1,8-bis(dimethylbismuthyl)-fluorenone-5-sulfonate,
1,8-dinitro-dibenzofuran-4,5-disulfonate,
4-sulfo-1,9-dinitro-dibenzofuran-5-sulfonate,
1,8-bis(trimethylstannyl)-dibenzofuran-4,5-disulfonate,
1,8-bis(dimethylantimonyl)-dibenzofuran-4,5-disulfonate,
1,8-bis(dimethylbismuthyl)-dibenzofuran-4,5-disulfonate,
4-sulfo-1,8-bis(trimethylstannyl)-dibenzofuran-5-sulfonate,
4-sulfo-1,8-bis(dimethylantimonyl)-dibenzofuran-5-sulfonate,
4-sulfo-1,8-bis(dimethylbismuthyl)-dibenzofuran-5-sulfonate,
1,8-dinitro-dibenzothiophene-4,5-disulfonate,
4-sulfo-1,9-dinitro-dibenzothiophene-5-sulfonate,
1,8-bis(trimethylstannyl)-dibenzothiophene-4,5-disulfonate,
1,8-bis(dimethylantimonyl)-dibenzothiophene-4,5-disulfonate,
1,8-bis(dimethylbismuthyl)-dibenzothiophene-4,5-disulfonate,
4-sulfo-1,8-bis(trimethylstannyl)-dibenzothiophene-5-sulfonate,
4-sulfo-1,8-bis(dimethylantimonyl)-dibenzothiophene-5-sulfonate,
4-sulfo-1,8-bis(dimethylbismuthyl)-dibenzothiophene-5-sulfonate,
1,8-dinitro-10-oxodibenzothiophene-4,5-disulfonate,
4-sulfo-1,9-dinitro-10-oxodibenzothiophene-5-sulfonate, 1,8-bis(trimethylstannyl)-10-oxodibenzothiophene-4,5-disulfonate,
1,8-bis(dimethylantimonyl)-10-oxodibenzothiophene-4,5-disulfonate,
1,8-bis(dimethylbismuthyl)-10-oxodibenzothiophene-4,5-disulfonate,
4-sulfo-1,8-bis(trimethylstannyl)-10-oxodibenzothiophene-5-sulfonate,
4-sulfo-1,8-bis(dimethylantimonyl)-10-oxodibenzothiophene-5-sulfonate,
4-sulfo-1,8-bis(dimethylbismuthyl)-10-oxodibenzothiophene-5-sulfonate,
1,8-dinitro-10,10-dioxodibenzothiophene-4,5-disulfonate,
4-sulfo-1,9-dinitro-10,10-dioxodibenzothiophene-5-sulfonate,
1,8-bis(trimethylstannyl)-10,10-dioxodibenzothiophene-4,5-disulfonate,
1,8-bis(dimethylantimonyl)-10,10-dioxodibenzothiophene-4,5-disulfonate,
1,8-bis(dimethylbismuthyl)-10,10-dioxodibenzothiophene-4,5-disulfonate,
4-sulfo-1,8-bis(trimethylstannyl)-10,10-dioxodibenzothiophene-5-sulfonate,
4-sulfo-1,8-bis(dimethylantimonyl)-10,10-dioxodibenzothiophene-5-sulfonate,
4-sulfo-1,8-bis(dimethylbismuthyl)-10,10-dioxodibenzothiophene-5-sulfonate,
4,6-dinitro-fluorene-1,9-disulfonate,
1-sulfo-4,6-dinitro-fluorene-9-sulfonate,
4,6-bis(trimethylstannyl)-fluorene-1,9-disulfonate,
4,6-bis(dimethylantimonyl)-fluorene-1,9-disulfonate,
4,6-bis(dimethylbismuthyl)-fluorene-1,9-disulfonate,
1-sulfo-4,6-bis(trimethylstannyl)-fluorene-9-sulfonate,
1-sulfo-4,6-bis(dimethylantimonyl)-fluorene-9-sulfonate,
1-sulfo-4,6-bis(dimethylbismuthyl)-fluorene-9-sulfonate,
4,6-dinitro-5,10-dihydroanthracene-1,9-disulfonate,
1-sulfo-4,6-dinitro-5,10-dihydroanthracene-9-sulfonate,
4,6-bis(trimethylstannyl)-5,10-dihydroanthracene-1,9-disulfonate,
4,6-bis(dimethylantimonyl)-5,10-dihydroanthracene-1,9-disulfonate,
4,6-bis(dimethylbismuthyl)-5,10-dihydroanthracene-1,9-disulfonate,
1-sulfo-4,6-bis(trimethylstannyl)-5,10-dihydroanthracene-9-sulfonate,
1-sulfo-4,6-bis(dimethylantimonyl)-5,10-dihydroanthracene-9-sulfonate,
1-sulfo-4,6-bis(dimethylbismuthyl)-5,10-dihydroanthracene-9-sulfonate,
1,9-dinitro-anthrone-4,6-disulfonate,
4-sulfo-1,9-dinitro-anthrone-6-sulfonate,
1,9-bis(trimethylstannyl)-anthrone-4,6-disulfonate,
1,9-bis(dimethylantimonyl)-anthrone-4,6-disulfonate,
1,9-bis(dimethylbismuthyl)-anthrone-4,6-disulfonate,
4-sulfo-1,9-bis(trimethylstannyl)-anthrone-6-sulfonate,
4-sulfo-1,9-bis(dimethylantimonyl)-anthrone-6-sulfonate,
4-sulfo-1,9-bis(dimethylbismuthyl)-anthrone-6-sulfonate,
1,9-dinitro-xanthene-4,6-disulfonate,
4-sulfo-1,9-dinitro-xanthene-6-sulfonate,
1,9-bis(trimethylstannyl)-xanthene-4,6-disulfonate,
1,9-bis(dimethylantimonyl)-xanthene-4,6-disulfonate,
1,9-bis(dimethylbismuthyl)-xanthene-4,6-disulfonate,
4-sulfo-1,9-bis(trimethylstannyl)-xanthene-6-sulfonate,
4-sulfo-1,9-bis(dimethylantimonyl)-xanthene-6-sulfonate,
4-sulfo-1,9-bis(dimethylbismuthyl)-xanthene-6-sulfonate,
1,9-dinitro-thioxanthene-4,6-disulfonate,
4-sulfo-1,9-dinitro-thioxanthene-6-sulfonate,
1,9-bis(trimethylstannyl)-thioxanthene-4,6-disulfonate,
1,9-bis(dimethylantimonyl)-thioxanthene-4,6-disulfonate,
1,9-bis(dimethylbismuthyl)-thioxanthene-4,6-disulfonate,
4-sulfo-1,9-bis(trimethylstannyl)-thioxanthene-6-sulfonate,
4-sulfo-1,9-bis(dimethylantimonyl)-thioxanthene-6-sulfonate,
4-sulfo-1,9-bis(dimethylbismuthyl)-thioxanthene-6-sulfonate,
1,9-dinitro-10-oxothioxanthene-4,6-disulfonate,
4-sulfo-1,9-dinitro-10-oxothioxanthene-6-sulfonate,
1,9-bis(trimethylstannyl)-10-oxothioxanthene-4,6-disulfonate,
1,9-bis(dimethylantimonyl)-10-oxothioxanthene-4,6-disulfonate,
1,9-bis(dimethylbismuthyl)-10-oxothioxanthene-4,6-disulfonate,
4-sulfo-1,9-bis(trimethylstannyl)-10-oxothioxanthene-6-sulfonate,
4-sulfo-1,9-bis(dimethylantimonyl)-10-oxothioxanthene-6-sulfonate,
4-sulfo-1,9-bis(dimethylbismuthyl)-10-oxothioxanthene-6-sulfonate,
1,9-dinitro-10,10-dioxothioxanthene-4,6-disulfonate,
4-sulfo-1,9-dinitro-10,10-dioxothioxanthene-6-sulfonate,
1,9-bis(trimethylstannyl)-10,10-dioxothioxanthene-4,6-disulfonate,
1,9-bis(dimethylantimonyl)-10,10-dioxothioxanthene-4,6-disulfonate,
1,9-bis(dimethylbismuthyl)-10,10-dioxothioxanthene-4,6-disulfonate,
4-sulfo-1,9-bis(trimethylstannyl)-10,10-dioxothioxanthene-6-sulfonate,
4-sulfo-1,9-bis(dimethylantimonyl)-10,10-dioxothioxanthene-6-sulfonate,
4-sulfo-1,9-bis(dimethylbismuthyl)-10,10-dioxothioxanthene-6-sulfonate,
4,6-dinitro-dibenzofuran-1,9-disulfonate,
1-sulfo-4,6-dinitro-dibenzofuran-9-sulfonate,
4,6-bis(trimethylstannyl)-dibenzofuran-1,9-disulfonate,
4,6-bis(dimethylantimonyl)-dibenzofuran-1,9-disulfonate,
4,6-bis(dimethylbismuthyl)-dibenzofuran-1,9-disulfonate,
1-sulfo-4,6-bis(trimethylstannyl)-dibenzofuran-9-sulfonate,
1-sulfo-4,6-bis(dimethylantimonyl)-dibenzofuran-9-sulfonate,
1-sulfo-4,6-bis(dimethylbismuthyl)-dibenzofuran-9-sulfonate,
4,6-dinitro-xanthene-1,9-disulfonate,
1-sulfo-4,6-dinitro-xanthene-9-sulfonate,
4,6-bis(trimethylstannyl)-xanthene-1,9-disulfonate,
4,6-bis(dimethylantimonyl)-xanthene-1,9-disulfonate,
4,6-bis(dimethylbismuthyl)-xanthene-1,9-disulfonate,
1-sulfo-4,6-bis(trimethylstannyl)-xanthene-9-sulfonate,
1-sulfo-4,6-bis(dimethylantimonyl)-xanthene-9-sulfonate,
1-sulfo-4,6-bis(dimethylbismuthyl)-xanthene-9-sulfonate,
1,9-dinitro-xanthone-4,6-disulfonate,
4-sulfo-1,9-dinitro-xanthone-6-sulfonate,
1,9-bis(trimethylstannyl)-xanthone-4,6-disulfonate,
1,9-bis(dimethylantimonyl)-xanthone-4,6-disulfonate,
1,9-bis(dimethylbismuthyl)-xanthone-4,6-disulfonate,
4-sulfo-1,9-bis(trimethylstannyl)-xanthone-6-sulfonate,
4-sulfo-1,9-bis(dimethylantimonyl)-xanthone-6-sulfonate,
4-sulfo-1,9-bis(dimethylbismuthyl)-xanthone-6-sulfonate,
4,6-dinitro-oxanthrene-1,9-disulfonate,
1-sulfo-4,6-dinitro-oxanthrene-9-sulfonate,
4,6-bis(trimethylstannyl)-oxanthrene-1,9-disulfonate,
4,6-bis(dimethylantimonyl)-oxanthrene-1,9-disulfonate,
4,6-bis(dimethylbismuthyl)-oxanthrene-1,9-disulfonate, 1-sulfo-4,6-bis(trimethylstannyl)-oxanthrene-9-sulfonate,
1-sulfo-4,6-bis(dimethylantimonyl)-oxanthrene-9-sulfonate,
1-sulfo-4,6-bis(dimethylbismuthyl)-oxanthrene-9-sulfonate,
1,9-dinitro-phenoxathiin-4,6-disulfonate,
4-sulfo-1,9-dinitro-phenoxathiin-6-sulfonate,
1,9-bis(trimethylstannyl)-phenoxathiin-4,6-disulfonate,
1,9-bis(dimethylantimonyl)-phenoxathiin-4,6-disulfonate,
1,9-bis(dimethylbismuthyl)-phenoxathiin-4,6-disulfonate,
4-sulfo-1,9-bis(trimethylstannyl)-phenoxathiin-6-sulfonate,
4-sulfo-1,9-bis(dimethylantimonyl)-phenoxathiin-6-sulfonate,
4-sulfo-1,9-bis(dimethylbismuthyl)-phenoxathiin-6-sulfonate,
1,9-dinitro-10-oxophenoxathiine-4,6-disulfonate,
4-sulfo-1,9-dinitro-10-oxophenoxathiine-6-sulfonate,
1,9-bis(trimethylstannyl)-10-oxophenoxathiine-4,6-disulfonate,
1,9-bis(dimethylantimonyl)-10-oxophenoxathiine-4,6-disulfonate,
1,9-bis(dimethylbismuthyl)-10-oxophenoxathiine-4,6-disulfonate,
4-sulfo-1,9-bis(trimethylstannyl)-10-oxophenoxathiine-6-sulfonate,
4-sulfo-1,9-bis(dimethylantimonyl)-10-oxophenoxathiine-6-sulfonate,
4-sulfo-1,9-bis(dimethylbismuthyl)-10-oxophenoxathiine-6-sulfonate,
1,9-dinitro-10,10-dioxophenoxathiine-4,6-disulfonate,
4-sulfo-1,9-dinitro-10,10-dioxophenoxathiine-6-sulfonate,
1,9-bis(trimethylstannyl)-10,10-dioxophenoxathiine-4,6-disulfonate,
1,9-bis(dimethylantimonyl)-10,10-dioxophenoxathiine-4,6-disulfonate,
1,9-bis(dimethylbismuthyl)-10,10-dioxophenoxathiine-4,6-disulfonate,
4-sulfo-1,9-bis(trimethylstannyl)-10,10-dioxophenoxathiine-6-sulfonate,
4-sulfo-1,9-bis(dimethylantimonyl)-10,10-dioxophenoxathiine-6-sulfonate,
4-sulfo-1,9-bis(dimethylbismuthyl)-10,10-dioxophenoxathiine-6-sulfonate,
4,6-dinitro-dibenzothiophene-1,9-disulfonate,
1-sulfo-4,6-dinitro-dibenzothiophene-9-sulfonate,
4,6-bis(trimethylstannyl)-dibenzothiophene-1,9-disulfonate,
4,6-bis(dimethylantimonyl)-dibenzothiophene-1,9-disulfonate,
4,6-bis(dimethylbismuthyl)-dibenzothiophene-1,9-disulfonate,
1-sulfo-4,6-bis(trimethylstannyl)-dibenzothiophene-9-sulfonate,
1-sulfo-4,6-bis(dimethylantimonyl)-dibenzothiophene-9-sulfonate,
1-sulfo-4,6-bis(dimethylbismuthyl)-dibenzothiophene-9-sulfonate,
4,6-dinitro-thioxanthene-1,9-disulfonate,
1-sulfo-4,6-dinitro-thioxanthene-9-sulfonate,
4,6-bis(trimethylstannyl)-thioxanthene-1,9-disulfonate,
4,6-bis(dimethylantimonyl)-thioxanthene-1,9-disulfonate,
4,6-bis(dimethylbismuthyl)-thioxanthene-1,9-disulfonate,
1-sulfo-4,6-bis(trimethylstannyl)-thioxanthene-9-sulfonate,
1-sulfo-4,6-bis(dimethylantimonyl)-thioxanthene-9-sulfonate,
1-sulfo-4,6-bis(dimethylbismuthyl)-thioxanthene-9-sulfonate,
1,9-dinitro-thioxanthone-4,6-disulfonate,
4-sulfo-1,9-dinitro-thioxanthone-6-sulfonate,
1,9-bis(trimethylstannyl)-thioxanthone-4,6-disulfonate,
1,9-bis(dimethylantimonyl)-thioxanthone-4,6-disulfonate,
1,9-bis(dimethylbismuthyl)-thioxanthone-4,6-disulfonate,
4-sulfo-1,9-bis(trimethylstannyl)-thioxanthone-6-sulfonate,
4-sulfo-1,9-bis(dimethylantimonyl)-thioxanthone-6-sulfonate,
4-sulfo-1,9-bis(dimethylbismuthyl)-thioxanthone-6-sulfonate,
4,6-dinitro-phenoxathiin-1,9-disulfonate,
1-sulfo-4,6-dinitro-phenoxathiin-9-sulfonate,
4,6-bis(trimethylstannyl)-phenoxathiin-1,9-disulfonate,
4,6-bis(dimethylantimonyl)-phenoxathiin-1,9-disulfonate,
4,6-bis(dimethylbismuthyl)-phenoxathiin-1,9-disulfonate,
1-sulfo-4,6-bis(trimethylstannyl)-phenoxathiin-9-sulfonate,
1-sulfo-4,6-bis(dimethylantimonyl)-phenoxathiin-9-sulfonate,
1-sulfo-4,6-bis(dimethylbismuthyl)-phenoxathiin-9-sulfonate,
4,6-dinitro-thianthrene-1,9-disulfonate,
1-sulfo-4,6-dinitro-thianthrene-9-sulfonate,
4,6-bis(trimethylstannyl)-thianthrene-1,9-disulfonate,
4,6-bis(dimethylantimonyl)-thianthrene-1,9-disulfonate,
4,6-bis(dimethylbismuthyl)-thianthrene-1,9-disulfonate,
1-sulfo-4,6-bis(trimethylstannyl)-thianthrene-9-sulfonate,
1-sulfo-4,6-bis(dimethylantimonyl)-thianthrene-9-sulfonate,
1-sulfo-4,6-bis(dimethylbismuthyl)-thianthrene-9-sulfonate,
4,6-dinitro-5-oxothianthrene-1,9-disulfonate,
1-sulfo-4,6-dinitro-5-oxothianthrene-9-sulfonate,
4,6-bis(trimethylstannyl)-5-oxothianthrene-1,9-disulfonate,
4,6-bis(dimethylantimonyl)-5-oxothianthrene-1,9-disulfonate,
4,6-bis(dimethylbismuthyl)-5-oxothianthrene-1,9-disulfonate,
1-sulfo-4,6-bis(trimethylstannyl)-5-oxothianthrene-9-sulfonate,
1-sulfo-4,6-bis(dimethylantimonyl)-5-oxothianthrene-9-sulfonate,
1-sulfo-4,6-bis(dimethylbismuthyl)-5-oxothianthrene-9-sulfonate,
4,6-dinitro-5,5-dioxothianthrene-1,9-disulfonate,
1-sulfo-4,6-dinitro-5,5-dioxothianthrene-9-sulfonate,
4,6-bis(trimethylstannyl)-5,5-dioxothianthrene-1,9-disulfonate,
4,6-bis(dimethylantimonyl)-5,5-dioxothianthrene-1,9-disulfonate,
4,6-bis(dimethylbismuthyl)-5,5-dioxothianthrene-1,9-disulfonate,
1-sulfo-4,6-bis(trimethylstannyl)-5,5-dioxothianthrene-9-sulfonate,
1-sulfo-4,6-bis(dimethylantimonyl)-5,5-dioxothianthrene-9-sulfonate, and
1-sulfo-4,6-bis(dimethylbismuthyl)-5,5-dioxothianthrene-9-sulfonate.

In a second aspect, the present invention relates to a photoacid generator comprising the polycyclic aromatic photoacid generator compound anion as specified herein and a cation. The cation is a conventional or typical cation used for photoacid generators, and there are numerous derivatives taught in the art. In one particular embodiment, the photoacid generator according to the present invention includes a combination of the photoacid generator compound anion according to the present invention with known fluorine free cations such as triphenylsulfonium, diphenyliodonium, phenylthiolanium, and derivatives thereof.

The photoacid generator compound cation's molecular structure in the PAG is chosen such that upon exposure, for example by DUV or by EUV radiation, the C—S bond in the sulfonium salt, or the C—I bond in the iodonium salt, or the C—S bond in the thiolanium salt is/are radically cleaved and the cation is internally stabilized. When the reaction (i.e., radical cleavage and stabilization) is completed, a proton ($H^+$) is released along with a degradation product of the cation, which is in a reduced oxidation state. The released proton ($H^+$) combines with the photoacid generator's anion, to form a Brønsted acid, that further participates in the photolithography process.

Figure 13:
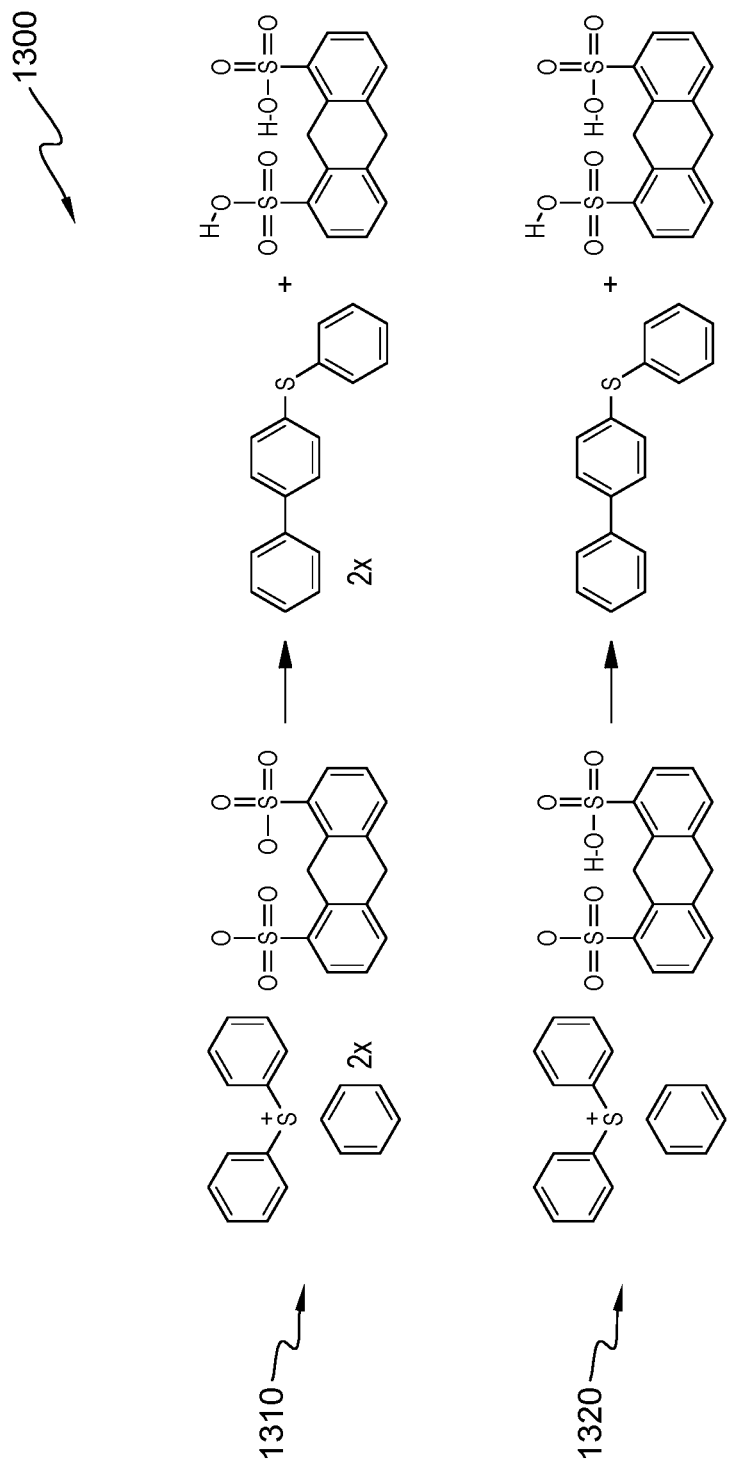
FIG. 13 depicts examples of PAG decomposition with acid generation according to an embodiment of the present invention.

FIG. 13 depicts exemplary PAGs with fluorine free anions according to the present invention: bis(triphenylsulfonium) 5,10-dihydroanthracene-1,9-disulfonate and triphenylsulfonium 1-sulfo-5,10-dihydroanthracene-9-sulfonate. Upon UV exposure, the C—S bond in the sulfonium salt undergoes radical cleavage and 5,10-dihydroanthracene-1,9-disulfonic acid is generated. FIG. 13, chemical reaction diagram 1300, depicts examples of PAG decomposition with acid generation according to an embodiment of the present invention, wherein examples of PAG decomposition with acid generation comprise: bis(triphenylsulfonium) 5,10-dihydroanthracene-1,9-disulfonate with 5,10-dihydroanthracene-1,9-disulfonic acid generation (1310), and triphenylsulfonium 1-sulfo-5,10-dihydroanthracene-9-sulfonate with 5,10-dihydroanthracene-1,9-disulfonic acid generation (1320).

In one particular embodiment, the photoacid generator according to the present invention is selected from the group consisting of:
bis(triphenylsulfonium) 5,10-dihydroanthracene-1,9-disulfonate,
triphenylsulfonium 1-sulfo-5,10-dihydroanthracene-9-sulfonate,
bis(diphenyliodonium) 5,10-dihydroanthracene-1,9-disulfonate,
diphenyliodonium 1-sulfo-5,10-dihydroanthracene-9-sulfonate,
bis(phenylthiolanium) 5,10-dihydroanthracene-1,9-disulfonate,
phenylthiolanium 1-sulfo-5,10-dihydroanthracene-9-sulfonate,
bis(triphenylsulfonium) 10,10-dioxothioxanthene-4,6-disulfonate,
triphenylsulfonium 4-sulfo-10,10-dioxothioxanthene-6-sulfonate,
bis(diphenyliodonium) 10,10-dioxothioxanthene-4,6-disulfonate,
diphenyliodonium 4-sulfo-10,10-dioxothioxanthene-6-sulfonate,
bis(phenylthiolanium) 10,10-dioxothioxanthene-4,6-disulfonate,
phenylthiolanium 4-sulfo-10,10-dioxothioxanthene-6-sulfonate,
bis(triphenylsulfonium) thianthrene-1,9-disulfonate,
triphenylsulfonium 1-sulfo-thianthrene-9-sulfonate,
bis(diphenyliodonium) thianthrene-1,9-disulfonate,
diphenyliodonium 1-sulfo-thianthrene-9-sulfonate,
bis(phenylthiolanium) thianthrene-1,9-disulfonate,
phenylthiolanium 1-sulfo-thianthrene-9-sulfonate,
bis(triphenylsulfonium) 5,5-dioxothianthrene-1,9-disulfonate,
triphenylsulfonium 1-sulfo-5,5-dioxothianthrene-9-sulfonate,
bis(diphenyliodonium) 5,5-dioxothianthrene-1,9-disulfonate,
diphenyliodonium 1-sulfo-5,5-dioxothianthrene-9-sulfonate,
bis(phenylthiolanium) 5,5-dioxothianthrene-1,9-disulfonate, and
phenylthiolanium 1-sulfo-5,5-dioxothianthrene-9-sulfonate.

The photoacid generator according to the present invention encompass in addition to the above specified polycyclic aromatic photoacid generator compound anions also derivatives, wherein the central cycle comprises the element having for 92 eV photons (EUV) an absorption cross section of at least $0.5 \times 10^7 \cdot cm^2/mol$ selected from the group consisting of tin, antimony, and bismuth; and/or wherein the element group substituent is on the first benzene moiety and/or second benzene moiety and is selected from the group consisting of stannyl group, antimonyl group, and bismuthyl group substituents; and/or wherein the electron withdrawing substituent is on the first benzene moiety and/or second benzene moiety and is selected from the group consisting of fluoro, perfluoroalkyl, alkylsulfinyl, alkylsulfonyl, nitro, cyano, as described before.

Figure 14:
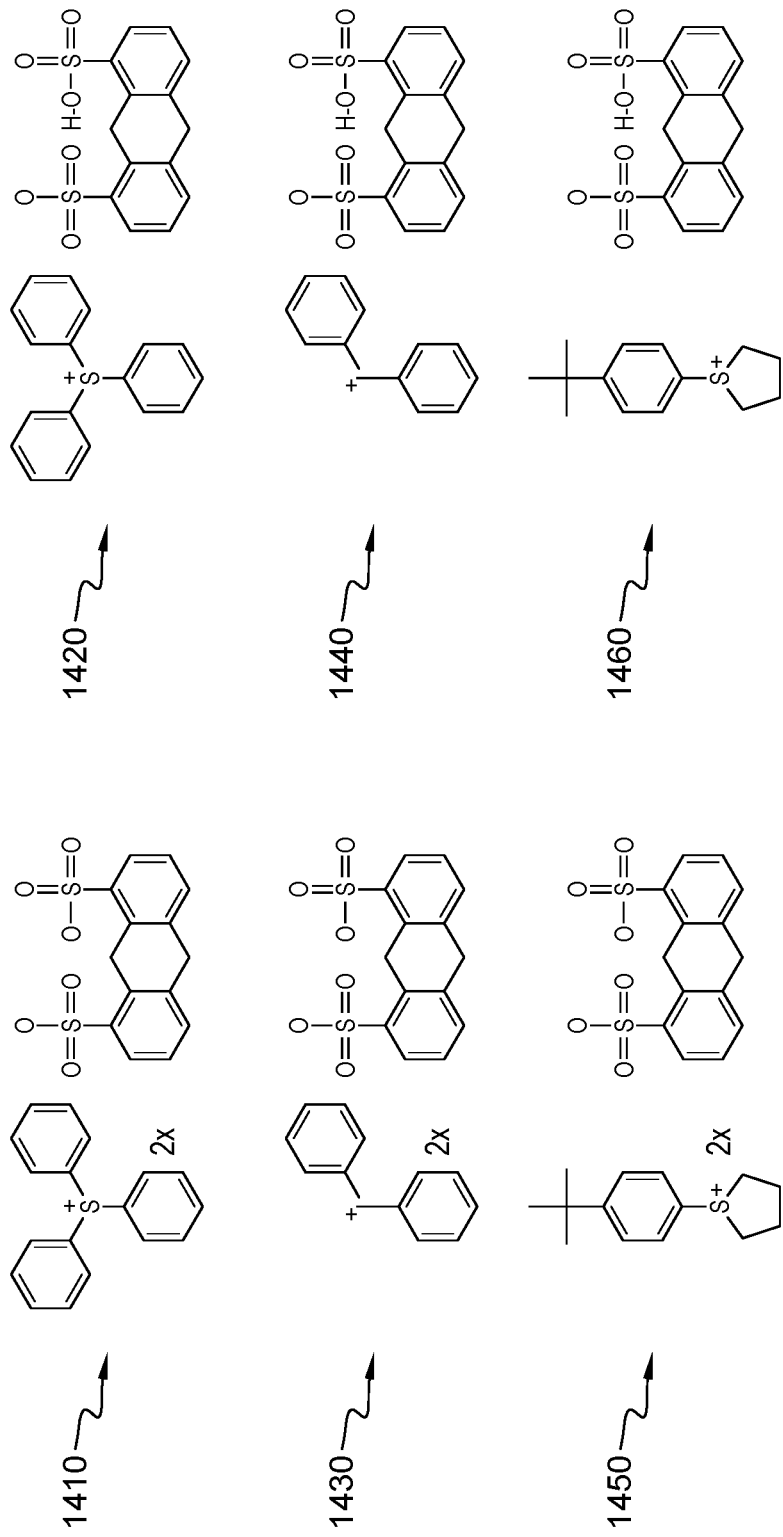
FIG. 14 depicts PAGs according to embodiments of the present invention.

FIG. 14 depicts PAGs according to embodiments of the present invention, wherein the PAGs comprise: bis(triphenylsulfonium) 5,10-dihydroanthracene-1,9-disulfonate (1410), triphenylsulfonium 1-sulfo-5,10-dihydroanthracene-9-sulfonate (1420), bis(diphenyliodonium) 5,10-dihydroanthracene-1,9-disulfonate (1430), diphenyliodonium 1-sulfo-5,10-dihydroanthracene-9-sulfonate (1440), bis(phenylthiolanium) 5,10-dihydroanthracene-1,9-disulfonate (1450), and phenylthiolanium 1-sulfo-5,10-dihydroanthracene-9-sulfonate (1460).

PAGs utilized in various embodiments of the present invention and including combinations of PAG anions according to embodiments of the present invention and known PAG cations as described before include: bis(triphenylsulfonium) 5,10-dihydroanthracene-1,9-disulfonate (1410), triphenylsulfonium 1-sulfo-5,10-dihydroanthracene-9-sulfonate (1420), bis(diphenyliodonium) 5,10-dihydroanthracene-1,9-disulfonate (1430), diphenyliodonium 1-sulfo-5,10-dihydroanthracene-9-sulfonate (1440), bis(phenylthiolanium) 5,10-dihydroanthracene-1,9-disulfonate (1450), and phenylthiolanium 1-sulfo-5,10-dihydroanthracene-9-sulfonate (1460), as shown in FIG. 14, and bis(triphenylsulfonium) 10,10-dioxothioxanthene-4,6-disulfonate, triphenylsulfonium 4-sulfo-10,10-dioxothioxanthene-6-sulfonate, bis(diphenyliodonium) 10,10-dioxothioxanthene-4,6-disulfonate, diphenyliodonium 4-sulfo-10,10-dioxothioxanthene-6-sulfonate, bis(phenylthiolanium) 10,10-dioxothioxanthene-4,6-disulfonate, phenylthiolanium 4-sulfo-10,10-dioxothioxanthene-6-sulfonate, bis(triphenylsulfonium) thianthrene-1,9-disulfonate, triphenylsulfonium 1-sulfo-thianthrene-9-sulfonate, bis(diphenyliodonium) thianthrene-1,9-disulfonate, diphenyliodonium 1-sulfo-thianthrene-9-sulfonate, bis(phenylthiolanium) thianthrene-1,9-disulfonate, phenylthiolanium 1-sulfo-thianthrene-9-sulfonate, bis(triphenylsulfonium) 5,5-dioxothianthrene-1,9-disulfonate, triphenylsulfonium 1-sulfo-5,5-dioxothianthrene-9-sulfonate, bis(diphenyliodonium) 5,5-dioxothianthrene-1,9-disulfonate, diphenyliodonium 1-sulfo-5,5-dioxothianthrene-9-sulfonate, bis(phenylthiolanium) 5,5-dioxothianthrene-1,9-disulfonate, phenylthiolanium 1-sulfo-5,5-dioxothianthrene-9-sulfonate; these PAGs generate upon UV exposure acids that have an acid dissociation constant similar to or even larger than that of trifluoromethanesulfonic acid.

Figure 15:
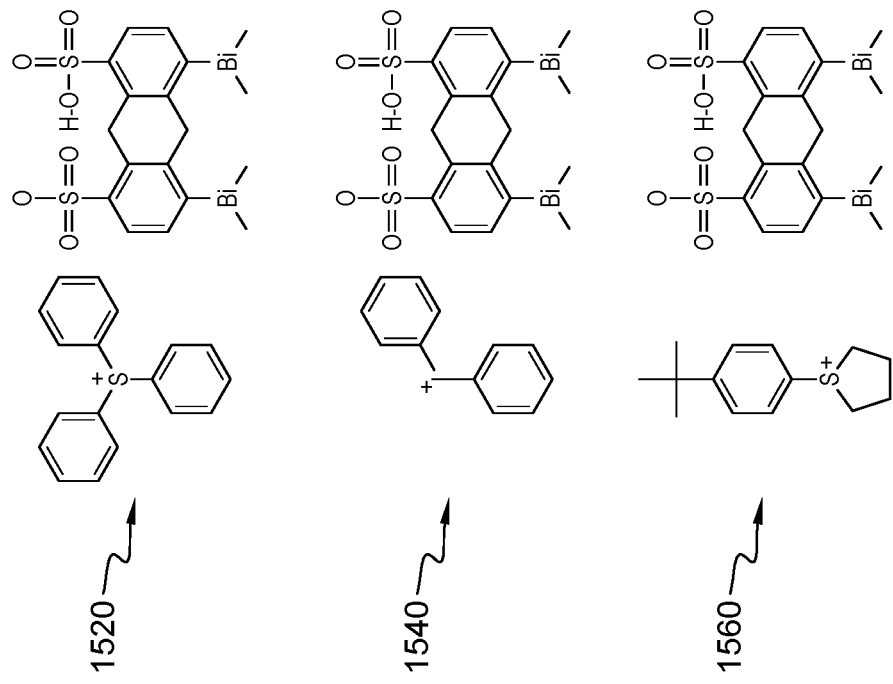
FIG. 15 an example of PAGs according to an embodiment of the present invention and especially suited for EUV lithography.
Figure 15:
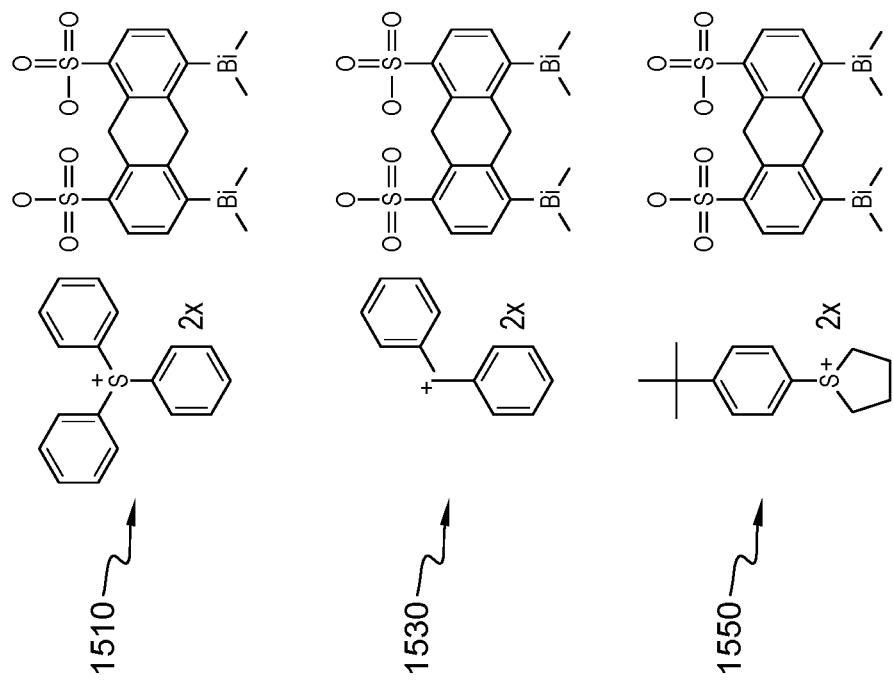

FIG. 15 an example of PAGs according to an embodiment of the present invention and especially suited for EUV lithography, wherein examples of PAGs especially suited for EUV lithography comprise: bis(triphenylsulfonium) 4,6-bis(dimethylbismuthyl)-5,10-dihydroanthracene-1,9-disulfonate (1510), triphenylsulfonium 1-sulfo-4,6-bis(dimethylbismuthyl)-5,10-dihydroanthracene-9-sulfonate (1520), bis(diphenyliodonium) 4,6-bis(dimethylbismuthyl)-5,10-dihydroanthracene-1,9-disulfonate (1530), diphenyliodonium 1-sulfo-4,6-bis(dimethylbismuthyl)-5,10-dihydroanthracene-9-sulfonate (1540), bis(phenylthiolanium) 4,6-bis(dimethylbismuthyl)-5,10-dihydroanthracene-1,9-disulfonate (1550), and phenylthiolanium 1-sulfo-4,6-bis(dimethylbismuthyl)-5,10-dihydroanthracene-9-sulfonate (1560).

In particular embodiments of PAGs according to the present invention and especially suited for EUV lithography, include combinations of PAG anions according to this invention, especially suited for EUV lithography, and known PAG cations such as triphenylsulfonium, diphenyliodonium, phenylthiolanium, and their derivatives. PAGs include bis(triphenylsulfonium) 4,6-bis(dimethylbismuthyl)-5,10-dihydroanthracene-1,9-disulfonate (1510), triphenylsulfonium 1-sulfo-4,6-bis(dimethylbismuthyl)-5,10-dihydroanthracene-9-sulfonate (1520), bis(diphenyliodonium) 4,6-bis(dimethylbismuthyl)-5,10-dihydroanthracene-1,9-disulfonate (1530), diphenyliodonium 1-sulfo-4,6-bis(dimethylbismuthyl)-5,10-dihydroanthracene-9-sulfonate (1540), bis(phenylthiolanium) 4,6-bis(dimethylbismuthyl)-5,10-dihydroanthracene-1,9-disulfonate (1550), and phenylthiolanium 1-sulfo-4,6-bis(dimethylbismuthyl)-5,10-dihydroanthracene-9-sulfonate (1560), as shown in FIG. 15, and bis(triphenylsulfonium) 1,9-bis(dimethylbismuthyl)-10,10-dioxothioxanthene-4,6-disulfonate, triphenylsulfonium 4-sulfo-1,9-bis(dimethylbismuthyl)-10,10-dioxothioxanthene-6-sulfonate, bis(diphenyliodonium) 1,9-bis(dimethylbismuthyl)-10,10-dioxothioxanthene-4,6-disulfonate, diphenyliodonium 4-sulfo-1,9-bis(dimethylbismuthyl)-10,10-dioxothioxanthene-6-sulfonate, bis(phenylthiolanium) 1,9-bis(dimethylbismuthyl)-10,10-dioxothioxanthene-4,6-disulfonate, phenylthiolanium 4-sulfo-1,9-bis(dimethylbismuthyl)-10,10-dioxothioxanthene-6-sulfonate, bis(triphenylsulfonium) 4,6-bis(dimethylbismuthyl)-thianthrene-1,9-disulfonate, triphenylsulfonium 1-sulfo-4,6-bis(dimethylbismuthyl)-thianthrene-9-sulfonate, bis(diphenyliodonium) 4,6-bis(dimethylbismuthyl)-thianthrene-1,9-disulfonate, diphenyliodonium 1-sulfo-4,6-bis(dimethylbismuthyl)-thianthrene-9-sulfonate, bis(phenylthiolanium) 4,6-bis(dimethylbismuthyl)-thianthrene-1,9-disulfonate, phenylthiolanium 1-sulfo-4,6-bis(dimethylbismuthyl)-thianthrene-9-sulfonate, bis(triphenylsulfonium) 4,6-bis(dimethylbismuthyl)-5,5-dioxothianthrene-1,9-disulfonate, triphenylsulfonium 1-sulfo-4,6-bis(dimethylbismuthyl)-5,5-dioxothianthrene-9-sulfonate, bis(diphenyliodonium) 4,6-bis(dimethylbismuthyl)-5,5-dioxothianthrene-1,9-disulfonate, diphenyliodonium 1-sulfo-4,6-bis(dimethylbismuthyl)-5,5-dioxothianthrene-9-sulfonate, bis(phenylthiolanium) 4,6-bis(dimethylbismuthyl)-5,5-dioxothianthrene-1,9-disulfonate, phenylthiolanium 1-sulfo-4,6-bis(dimethylbismuthyl)-5,5-dioxothianthrene-9-sulfonate; these PAGs generate upon UV exposure acids that have an acid dissociation constant similar to or even larger than that of trifluoromethanesulfonic acid.

However, persons with an ordinary skill in the art will realize that in the photoreactions described in detail above also other, i.e., modified, photoacid generator compound anions according to the present invention with alternative substituents on the first and/or second benzene moieties, such as alkyl, aryl, fluoro, perfluoroalkyl, alkylsulfinyl, alkylsulfonyl, nitro, or cyano substituents, can be used. Additionally, persons with an ordinary skill in the art will realize that in the photoreactions described in detail above also other, i.e., modified, photoacid generator compound cations, e.g., substituted cations, complex cations, etc., can be used.

The synthesis of the PAG according to the present invention is described exemplary for the PAG bis(triphenylsulfonium) 5,10-dihydroanthracene-1,9-disulfonate. First, to a solution of dipotassium anthraquinone-1,8-disulfonate and 18-crown-6 ether in acetone was added cyanuric chloride. The mixture was heated under reflux for a few hours to yield anthraquinone-1,8-disulfonyl chloride. To a solution anthraquinone-1,8-sulfonyl chloride in pyridine was added ethanol. The mixture was stirred for a few hours to yield anthraquinone-1,8-diethylsulfonate. Anthraquinone-1,8-diethylsulfonate, red phosphorus, and iodine were placed in an ampule and HI in water was added. The ampule was sealed and heated to 140° C. for a few days to yield 5,10-dihydroanthracene-1,9-diethylsulfonate. Hydrolyses of 5,10-dihydroanthracene-1,9-diethylsulfonate with NaOH yielded sodium 5,10-dihydroanthracene-1,9-disulfonate. Then to dichloromethane was added an aqueous solution of triphenylsulfonium chloride and sodium 5,10-dihydroanthracene-1,9-disulfonate, followed by stirring. The organic layer was separated and washed with water. The organic layer was concentrated, and the final bis(triphenylsulfonium) 5,10-dihydroanthracene-1,9-disulfonate compound was obtained by crystallization. People with an ordinary skill in the art will realize that other photoacid generators according to the present invention can be synthesized along the same lines.

Due to their distinguished properties as described above, the photoacid generator comprising the photoacid generator compound anion according to the present invention, can be formulated into polymer compositions that are useful in lithographic processes.

Hence, in a further aspect, the present invention relates to a photoresist composition, comprising: (a) a photoacid generator according to the present invention; and (b) an acid labile polymer.

The acid labile polymer is capable of undergoing chemical transformations upon exposure of the photoresist composition, in particular DUV irradiation or EUV irradiation, whereby a differential in the solubility of the polymer in either the exposed regions or the unexposed regions is created. In such a polymer, the acid sensitivity exists because of the presence of acid sensitive side chains that are bonded to the polymer backbone. Such acid sensitive polymers including acid sensitive side chains are conventionally.

The acid labile imaging polymer used according to embodiments of the present invention is selected from poly(hydroxystyrene), poly(styrene), poly(t-butyl methacrylate), and poly(2-Ethyl-2-adamantyl-methacrylate) for DUV lithography or from a copolymer such as poly(p-hydroxy styrene)-r-poly(t-butyl acrylate) and a terpolymer such as poly(p-hydroxy styrene)-r-poly(styrene)-r-poly(t-butyl acrylate) for EUV lithography.

The content of the photoacid generator according to the present invention in the photoresist composition is 1 to 30% by weight or 5 to 20% by weight, based on the total weight of the photoresist composition.

The photoresist compositions of the invention contain a solvent which is capable of dissolving the acid sensitive imaging polymer and the photoacid generator. Examples of such solvents comprise, but are not limited to, ethers, glycol ethers, aromatic hydrocarbons, ketones, esters and the like.

A solvent system including a mixture of the aforementioned solvents is also contemplated herein. Suitable glycol ethers include 2-methoxyethyl ether (diglyme), ethylene glycol monomethyl ether, propylene glycol monomethyl ether, propylene glycol monomethylether acetate (PGMEA) and the like. Suitable aromatic hydrocarbon solvents include toluene, xylene, and benzene. Examples of ketones include methylisobutylketone, 2-heptanone, cycloheptanone, and cyclohexanone. An example of an ether solvent is tetrahydrofuran, whereas ethyl lactate and ethoxy ethyl propionate are examples of ester solvents that may be employed herein.

In addition to the above components, the photoresist composition may also include other components such as a base quencher, a photosensitizer, a pigment, a filler, an antistatic agent, a flame retardant, a defoaming agent, a light stabilizer, an antioxidant, or other additives. If desired, combinations or mixtures of these other components may be used.

The chemically amplified photoresists for DUV and for EUV lithography that comprise the new PAGs comprising the new polycyclic aromatic photoacid generator compound anion are fluorine free.

The new PAGs comprising the new polycyclic aromatic photoacid generator compound anions according to the present invention generate upon UV exposure fluorine free acids that have a high acid dissociation constant.

The chemically amplified photoresists for DUV and for EUV lithography that comprise the new PAGs comprising the new polycyclic aromatic photoacid generator compound anion may have a material's toxicity and chemical waste advantage.

The chemically amplified photoresists for EUV lithography that comprise the new PAGs comprising the new polycyclic aromatic photoacid generator compound anion may have a high absorption cross section for photons in the EUV to increase the sensitivity of chemical amplified photoresists for EUV lithography.

The chemically amplified photoresists for EUV lithography that comprise the new PAGs according to the present invention also pose limited process-integration risks because the process flow in the fab's photobay is unchanged.

In a further aspect, the present invention also encompasses a method of using the photoresist composition of the invention for generating an acid. Said method comprises: (i) applying a photoresist composition of the invention, containing the photoacid generator according to the invention, to a substrate; and (ii) irradiating patternwise the photoresist composition with an energy ray to cause the photoacid generator to generate an acid.

As substrate in the present invention is suitable any substrate conventionally used in processes involving photoresists. For example, the substrate can be silicon, silicon oxide, aluminium, aluminium oxide, gallium arsenide, ceramic, quartz, copper or any combination thereof, including multilayers.

In one particular embodiment of the method according to the present invention, the energy ray with which the patternwise irradiation of the photoresist composition is conducted, is a DUV irradiation or an EUV irradiation.

In a further aspect, the present invention also encompasses a method for using the photoresist composition of the invention to form patterned material features on a substrate comprising a material surface which may comprise a metal conductor layer, a ceramic insulator layer, a semiconductor layer or other material depending on the stage of the manufacture process and the desired material set for the end product. The photoresist composition of the invention is especially useful for EUV lithographic processes used in the manufacture of integrated circuits on semiconductor substrates. The photoresist composition of the invention used in lithographic processes create patterned material layer structures such as metal wiring lines, holes for contacts or vias, insulation sections (e.g., damascene trenches or shallow trench isolation), trenches for capacitor structures, ion implanted semiconductor structures for transistors, and the like as might be used in integrated circuit devices.

After exposure, the photoresist structure with the desired pattern is obtained or developed by contacting the photoresist layer with an aqueous alkaline solution which selectively dissolves the areas of the photoresist which were exposed to radiation in the case of a positive photoresist (or the unexposed areas in the case of a negative photoresist). Some aqueous alkaline solutions or developers comprise aqueous solutions of tetramethyl ammonium hydroxide. The resulting lithographic structure on the substrate is then typically dried to remove any remaining developer. If a top coat has been used, it can be dissolved by the developer in this step.

The pattern from the photoresist structure may then be transferred to the exposed portions of underlying material of the substrate by etching with a suitable etchant using techniques known in the art. In one embodiment the transfer is done by reactive ion etching or by wet etching. Once the desired pattern transfer has taken place, any remaining photoresist may be removed using conventional stripping techniques. Alternatively, the pattern may be transferred by ion implantation to form a pattern of ion implanted material.

In one particular embodiment of the method according to the present invention, the energy ray with which the patternwise irradiation of the photoresist composition is conducted, is a DUV irradiation or an EUV irradiation.

What is claimed is:

1. A photoacid generator comprising a cation and a polycyclic aromatic photoacid generator compound anion of a general formula, wherein the general formula comprises (first benzene moiety-X-second benzene moiety)$^-$, and wherein the cation is selected from the group consisting of triphenylsulfonium, diphenyliodonium, phenylthiolanium, and derivatives thereof and wherein:

X represents a central cycle;

the first benzene moiety is substituted with a first sulfonate group and the second benzene moiety is substituted with a second sulfonate group; or the first benzene moiety is substituted with a sulfonate group and the second benzene moiety is substituted with a sulfonic acid group; and the first sulfonate group and the second sulfonate group or the first sulfonate group and the sulfonic acid group are arranged on said first and second benzene moiety such that their orbitals can interact with each other.

2. The polycyclic aromatic photoacid generator compound anion according to claim 1, wherein the first benzene moiety and the second benzene moiety are linked to the central cycle in order to form a condensed ring system, in particular, wherein the condensed ring system is a linear condensed ring system.

3. The polycyclic aromatic photoacid generator compound anion according to claim 2, wherein the condensed ring system is selected from the group consisting of:

biphenylene,
fluorene,
fluorenone,
dibenzofuran,
dibenzothiophene, dibenzothiophene-10-oxide,
dibenzothiophene-10,10-dioxide,
5,10-dihydroanthracene,
anthrone,
xanthene,
thioxanthene,
thioxanthene-10-oxide,
thioxanthene-10,10-dioxide,
dibenzofuran,
xanthone,
oxanthrene,
phenoxathiin,
phenoxathiin-10-oxide,
phenoxathiin-10,10-dioxide,
dibenzothiphene,
thioxanthene,
thioxanthone,
thianthrene,
thianthrene-5-oxide, and
thianthrene-5,5-dioxide.

4. The polycyclic aromatic photoacid generator compound anion according to claim 1, wherein the central cycle is a four membered, five membered, six membered, seven membered, or eight membered cycle, in particular a five membered or six membered cycle.

5. The polycyclic aromatic photoacid generator compound anion according to claim 1, wherein in the central cycle at least one atom which is not chemically bonded to the first benzene moiety and to the second benzene moiety is a heteroatom selected from the group consisting of O and S, or wherein the central cycle is functionalized by a group selected from the group consisting of carbonyl, sulfinyl, and sulfonyl, or wherein in the central cycle at least one atom which is not chemically bonded to the first benzene moiety and to the second benzene moiety is a heteroatom selected from the group consisting of O and S and the central cycle is functionalized by a group selected from the group consisting of carbonyl, sulfinyl, and sulfonyl.

6. The polycyclic aromatic photoacid generator compound anion according to claim 1, wherein the central cycle is derived from compounds selected from the group consisting of:
cyclobutane, cyclopentane, cyclohexane, cycloheptane, cyclooctane,
tetrahydrofuran (five-membered cycle with O),
tetrahydrothiophene (five-membered cycle with S),
cyclopentanone (five-membered cycle with carbonyl),
tetrahydrothiophene-1-oxide (five-membered cycle with sulfinyl),
tetrahydrothiophene-1,1-dioxide (five-membered cycle with sulfonyl),
tetrahydropyran (six-membered cycle with O),
tetrahydrothiopyran (six-membered cycle with S),
cyclohexanone (six-membered cycle with carbonyl),
tetrahydrothiopyran-1-oxide (six-membered cycle with sulfinyl),
tetrahydrothiopyran-1,1-dioxide (six-membered cycle with sulfonyl),
1,4-oxathiane (six-membered cycle with O and S),
4-tetrahydropyranone (six-membered cycle with O and carbonyl),
1,4-oxathiane-4-oxide (six-membered cycle with O and sulfinyl),
1,4-oxathiane-4,4-dioxide (six-membered cycle with O and sulfonyl),
4-tetrahydrothiopyranone (six-membered cycle with S and carbonyl),
1,4-dithiane-1-oxide (six-membered cycle with S and sulfinyl),
1,4-dithiane-1,1-dioxide (six-membered cycle with S and sulfonyl),
1,4-dioxane (six-membered cycle with 2 O), and
1,4-dithiane (six-membered cycle with 2 S).

7. The polycyclic aromatic photoacid generator compound anion according to claim 1, wherein the first and the second sulfonate group or the sulfonate group and the sulfonic acid group are arranged on the same side of the planar of the condensed ring system, in particular wherein the first and the second sulfonate group or the sulfonate group and the sulfonic acid group are arranged on the same side of the planar of the condensed ring system and are linked to the first carbon atom of the first and second benzene moieties adjacent to the central cycle.

8. The polycyclic aromatic photoacid generator compound anion according to claim 7, wherein the first or the second benzene moiety/moieties is/are substituted with an electron withdrawing group selected from the group consisting of fluoro, perfluoroalkyl, alkylsulfinyl, alkylsulfonyl, nitro, and cyano, in particular wherein the electron withdrawing group is selected from the group consisting of nitro and cyano.

9. The polycyclic aromatic photoacid generator compound anion according to claim 1, wherein the central cycle comprises an element having for 92 eV photons (EUV) an absorption cross section of at least $0.5 \times 10^7 \cdot cm^2/mol$; or wherein the first or second benzene moiety is substituted with a group comprising an element having for 92 eV photons (EUV) an absorption cross section of at least $0.5 \times 10^7 \cdot cm^2/mol$; or wherein the central cycle comprises an element having for 92 eV photons (EUV) an absorption cross section of at least $0.5 \times 10^7 \cdot cm^2/mol$ and the first and second benzene moiety is substituted with a group comprising an element having for 92 eV photons (EUV) an absorption cross section of at least $0.5 \times 10^7 \cdot cm^2/mol$.

10. The polycyclic aromatic photoacid generator compound anion according to claim 9, wherein the element is selected from the group consisting of the elements In, Sn, Sb, Te, Tl, Pb, and Bi, in particular wherein the element is selected from the group consisting of the elements Sn, Sb, and Bi.

11. The polycyclic aromatic photoacid generator compound anion according to claim 10, wherein the electron withdrawing group substituent and the element group substituent comprising an element having for 92 eV photons (EUV) an absorption cross section of at least $0.5 \times 10^7 \cdot cm^2/mol$ substituent is in ortho- and para-position to the first sulfonate group and the second sulfonate group of the first and second benzene moiety; or is in ortho- or para-position to the sulfonate group and the sulfonic acid group of the first or second benzene moiety.

12. The polycyclic aromatic photoacid generator compound anion according to claim 1, wherein the polycyclic aromatic photoacid generator compound anion is selected from the group consisting of:
biphenylene-1,8-disulfonate,
fluorene-4,5-disulfonate,
fluorenone-4,5-disulfonate,
dibenzofuran-4,5-disulfonate,
dibenzothiophene-4,5-disulfonate,
10-oxodibenzothiophene-4,5-disulfonate,
10,10-dioxodibenzothiophene-4,5-disulfonate,
fluorene-1,9-disulfonate,
5,10-dihydroanthracene-1,9-disulfonate,
anthrone-4,6-disulfonate, xanthene-4,6-disulfonate,
thioxanthene-4,6-disulfonate,
10-oxothioxanthene-4,6-disulfonate,
10,10-dioxothioxanthene-4,6-disulfonate,
dibenzofuran-1,9-disulfonate,
xanthene-1,9-disulfonate,
xanthone-4,6-disulfonate,
oxanthrene-1,9-disulfonate,
phenoxathiin-4,6-disulfonate,
10-oxophenoxathiine-4,6-disulfonate,
10,10-dioxophenoxathiine-4,6-disulfonate,
dibenzothiophene-1,9-disulfonate,
thioxanthene-1,9-disulfonate,
thioxanthone-4,6-disulfonate,
phenoxathiin-1,9-disulfonate,
thianthrene-1,9-disulfonate,
5-oxothianthrene-1,9-disulfonate,
5,5-dioxothianthrene-1,9-disulfonate,
1-sulfo-biphenylene-8-sulfonate,
4-sulfo-fluorene-5-sulfonate,
4-sulfo-fluorenone-5-sulfonate,
4-sulfo-dibenzofuran-5-sulfonate,
4-sulfo-dibenzothiophene-5-sulfonate,
4-sulfo-10-oxodibenzothiophene-5-sulfonate,
4-sulfo-10,10-dioxodibenzothiophene-5-sulfonate,
1-sulfo-fluorene-9-sulfonate,
1-sulfo-5,10-dihydroanthracene-9-sulfonate,
4-sulfo-anthrone-6-sulfonate,
4-sulfo-xanthene-6-sulfonate,
4-sulfo-thioxanthene-6-sulfonate,
4-sulfo-10-oxothioxanthene-6-sulfonate,
4-sulfo-10,10-dioxothioxanthene-6-sulfonate,
1-sulfo-dibenzofuran-9-sulfonate,
1-sulfo-xanthene-9-sulfonate,
4-sulfo-xanthone-6-sulfonate,
1-sulfo-oxanthrene-9-sulfonate,
4-sulfo-phenoxathiin-6-sulfonate,
4-sulfo-10-oxophenoxathiine-6-sulfonate,
4-sulfo-10,10-dioxophenoxathiine-6-sulfonate,
1-sulfo-dibenzothiophene-9-sulfonate,
1-sulfo-thioxanthene-9-sulfonate,
4-sulfo-thioxanthone-6-sulfonate,
1-sulfo-phenoxathiin-9-sulfonate,
1-sulfo-thianthrene-9-sulfonate,
1-sulfo-5-oxothianthrene-9-sulfonate,
1-sulfo-5,5-dioxothianthrene-9-sulfonate, and
derivatives of the afore-said polycyclic aromatic photoacid generator compound anions, wherein the central cycle comprises the element having for 92 eV photons (EUV) an absorption cross section of at least 0.5× $10^7 \cdot cm^2/mol$ selected from the group consisting of tin, antimony, and bismuth; and wherein the element group substituent is on the first benzene moiety and second benzene moiety and is selected from the group consisting of stannyl group, antimonyl group, and bismuthyl group substituents; and wherein the electron withdrawing substituent is on the first benzene moiety or second benzene moiety and is selected from the group consisting of fluoro, perfluoroalkyl, alkylsulfinyl, alkylsulfonyl, nitro, and cyano.

13. The polycyclic aromatic photoacid generator compound anion according to claim 12, wherein the polycyclic aromatic photoacid generator compound anion is selected from the group consisting of:
4,6-dinitro-5,10-dihydroanthracene-1,9-disulfonate,
1-sulfo-4,6-dinitro-5,10-dihydroanthracene-9-sulfonate,
4,6-bis(trimethylstannyl)-5,10-dihydroanthracene-1,9-disulfonate,
4,6-bis(dimethylantimonyl)-5,10-dihydroanthracene-1,9-disulfonate,
4,6-bis(dimethylbismuthyl)-5,10-dihydroanthracene-1,9-disulfonate,
1-sulfo-4,6-bis(trimethylstannyl)-5,10-dihydroanthracene-9-sulfonate,
1-sulfo-4,6-bis(dimethylantimonyl)-5,10-dihydroanthracene-9-sulfonate,
1-sulfo-4,6-bis(dimethylbismuthyl)-5,10-dihydroanthracene-9-sulfonate,
1,9-dinitro-10,10-dioxothioxanthene-4,6-disulfonate,
4-sulfo-1,9-dinitro-10,10-dioxothioxanthene-6-sulfonate,
1,9-bis(trimethylstannyl)-10,10-dioxothioxanthene-4,6-disulfonate,
1,9-bis(dimethylantimonyl)-10,10-dioxothioxanthene-4,6-disulfonate,
1,9-bis(dimethylbismuthyl)-10,10-dioxothioxanthene-4,6-disulfonate,
4-sulfo-1,9-bis(trimethylstannyl)-10,10-dioxothioxanthene-6-sulfonate,
4-sulfo-1,9-bis(dimethylantimonyl)-10,10-dioxothioxanthene-6-sulfonate,
4-sulfo-1,9-bis(dimethylbismuthyl)-10,10-dioxothioxanthene-6-sulfonate,
4,6-dinitro-thianthrene-1,9-disulfonate,
1-sulfo-4,6-dinitro-thianthrene-9-sulfonate,
4,6-bis(trimethylstannyl)-thianthrene-1,9-disulfonate,
4,6-bis(dimethylantimonyl)-thianthrene-1,9-disulfonate,
4,6-bis(dimethylbismuthyl)-thianthrene-1,9-disulfonate,
1-sulfo-4,6-bis(trimethylstannyl)-thianthrene-9-sulfonate,
1-sulfo-4,6-bis(dimethylantimonyl)-thianthrene-9-sulfonate,
1-sulfo-4,6-bis(dimethylbismuthyl)-thianthrene-9-sulfonate,
4,6-dinitro-5,5-dioxothianthrene-1,9-disulfonate,
1-sulfo-4,6-dinitro-5,5-dioxothianthrene-9-sulfonate,
4,6-bis(trimethylstannyl)-5,5-dioxothianthrene-1,9-disulfonate,
4,6-bis(dimethylantimonyl)-5,5-dioxothianthrene-1,9-disulfonate,
4,6-bis(dimethylbismuthyl)-5,5-dioxothianthrene-1,9-disulfonate,
1-sulfo-4,6-bis(trimethylstannyl)-5,5-dioxothianthrene-9-sulfonate,
1-sulfo-4,6-bis(dimethylantimonyl)-5,5-dioxothianthrene-9-sulfonate, and
1-sulfo-4,6-bis(dimethylbismuthyl)-5,5-dioxothianthrene-9-sulfonate.

14. The photoacid generator according to claim 1, selected from the group consisting of:
bis(triphenylsulfonium) 5,10-dihydroanthracene-1,9-disulfonate,
triphenylsulfonium 1-sulfo-5,10-dihydroanthracene-9-sulfonate,
bis(diphenyliodonium) 5,10-dihydroanthracene-1,9-disulfonate,
diphenyliodonium 1-sulfo-5,10-dihydroanthracene-9-sulfonate,
bis(phenylthiolanium) 5,10-dihydroanthracene-1,9-disulfonate,
phenylthiolanium 1-sulfo-5,10-dihydroanthracene-9-sulfonate,
bis(triphenylsulfonium) 10,10-dioxothioxanthene-4,6-disulfonate, triphenylsulfonium 4-sulfo-10,10-dioxothioxanthene-6-sulfonate,
bis(diphenyliodonium) 10,10-dioxothioxanthene-4,6-disulfonate,
diphenyliodonium 4-sulfo-10,10-dioxothioxanthene-6-sulfonate,
bis(phenylthiolanium) 10,10-dioxothioxanthene-4,6-disulfonate,
phenylthiolanium 4-sulfo-10,10-dioxothioxanthene-6-sulfonate,
bis(triphenylsulfonium) thianthrene-1,9-disulfonate,
triphenylsulfonium 1-sulfo-thianthrene-9-sulfonate,
bis(diphenyliodonium) thianthrene-1,9-disulfonate,
diphenyliodonium 1-sulfo-thianthrene-9-sulfonate,
bis(phenylthiolanium) thianthrene-1,9-disulfonate,
phenylthiolanium 1-sulfo-thianthrene-9-sulfonate,
bis(triphenylsulfonium) 5,5-dioxothianthrene-1,9-disulfonate,
triphenylsulfonium 1-sulfo-5,5-dioxothianthrene-9-sulfonate,
bis(diphenyliodonium) 5,5-dioxothianthrene-1,9-disulfonate,
diphenyliodonium 1-sulfo-5,5-dioxothianthrene-9-sulfonate,
bis(phenylthiolanium) 5,5-dioxothianthrene-1,9-disulfonate,
phenylthiolanium 1-sulfo-5,5-dioxothianthrene-9-sulfonate, and
derivatives of the afore-said polycyclic aromatic photoacid generator compound anions, wherein the central cycle comprises the element having for 92 eV photons (EUV) an absorption cross section of at least $0.5 \times 10^7 \cdot cm^2/mol$ selected from the group consisting of tin, antimony, and bismuth; and wherein the element group substituent is on the first benzene moiety and second benzene moiety and is selected from the group consisting of stannyl group, antimonyl group, and bismuthyl group substituents; and wherein the electron withdrawing substituent is on the first benzene moiety or second benzene moiety and is selected from the group consisting of fluoro, perfluoroalkyl, alkylsulfinyl, alkylsulfonyl, nitro, and cyano.

15. A photoresist composition comprising:
an acid labile polymer; and
a photoacid generator comprising polycyclic aromatic photoacid generator compound anion and a cation, wherein the cation is selected from the group consisting of triphenylsulfonium, diphenyliodonium, phenylthiolanium, and derivatives thereof, and wherein the polycyclic aromatic photoacid generator compound anion of comprises a general formula, wherein the general formula comprises (first benzene moiety-X-second benzene moiety)⁻, and wherein:
X represents a central cycle;
the first benzene moiety is substituted with a first sulfonate group and the second benzene moiety is substituted with a second sulfonate group; or
the first benzene moiety is substituted with a sulfonate group and the second benzene moiety is substituted with a sulfonic acid group; and
the first sulfonate group and the second sulfonate group or the first sulfonate group and the sulfonic acid group are arranged on said first and second benzene moiety such that their orbitals can interact with each other.

16. The photoresist composition according to claim 15, comprising the photoacid generator in an amount of 1 to 30% by weight, based on the total weight of the photoresist composition.

17. A method of generating an acid, wherein the method comprises:
applying a photoresist composition to a substrate, wherein the photoacid generator comprising polycyclic aromatic photoacid generator compound anion and a cation, wherein the cation is selected from the group consisting of triphenylsulfonium, diphenyliodonium, phenylthiolanium, and derivatives thereof and an acid labile polymer, and wherein the polycyclic aromatic photoacid generator compound anion of comprises a general formula, wherein the general formula comprises (first benzene moiety-X-second benzene moiety)⁻, and wherein X represents a central cycle; and
irradiating the photoresist composition with an energy ray to cause the photoacid generator to generate an acid.

18. A method of forming a patterned materials feature on a substrate, wherein the method comprises:
providing a material surface on a substrate;
forming a layer of the photoresist composition over said material surface, wherein the photoacid generator comprising polycyclic aromatic photoacid generator compound anion and a cation, wherein the cation is selected from the group consisting of triphenylsulfonium, diphenyliodonium, phenylthiolanium, and derivatives thereof and an acidlabile polymer, and wherein the polycyclic aromatic photoacid generator compound anion of comprises a general formula, wherein the general formula comprises (first benzene moiety-X-second benzene moiety)⁻, and wherein X represents a central cycle;
patternwise irradiating the photoresist layer with an energy ray thereby creating a pattern of radiation-exposed regions in said photoresist layer;
selectively removing portions of said photoresist layer to form exposed portions of said material surface; and
etching or ion implanting said exposed portions of said material, thereby forming said patterned material feature.

19. The method according to claim 18, wherein the energy ray is a deep ultraviolet (DUV) irradiation or an extreme ultraviolet (EUV) irradiation.

* * * * *